United States Patent
Chiriva-Internati et al.

(10) Patent No.: US 10,717,774 B2
(45) Date of Patent: Jul. 21, 2020

(54) COMPOSITIONS AND METHODS FOR TREATING CANCERS

(71) Applicant: Kiromic, Inc., Houston, TX (US)

(72) Inventors: Maurizio Chiriva-Internati, Lubbock, TX (US); Leonardo Mirandola, Houston, TX (US)

(73) Assignee: KIROMIC, INC., Houston, TX (US)

( * ) Notice: Subject to any disclaimer, the term of this patent is extended or adjusted under 35 U.S.C. 154(b) by 0 days.

(21) Appl. No.: 16/082,363

(22) PCT Filed: Mar. 13, 2017

(86) PCT No.: PCT/US2017/022168
§ 371 (c)(1),
(2) Date: Sep. 5, 2018

(87) PCT Pub. No.: WO2017/160761
PCT Pub. Date: Sep. 21, 2017

(65) Prior Publication Data
US 2019/0031732 A1 Jan. 31, 2019

Related U.S. Application Data

(60) Provisional application No. 62/308,045, filed on Mar. 14, 2016.

(51) Int. Cl.
| | | |
|---|---|---|
| *A61K 38/17* | (2006.01) | |
| *A61P 35/00* | (2006.01) | |
| *A61P 35/02* | (2006.01) | |
| *G01N 33/574* | (2006.01) | |
| *A61K 38/00* | (2006.01) | |
| *C07K 14/47* | (2006.01) | |
| *A61K 45/06* | (2006.01) | |
| *A61K 31/7064* | (2006.01) | |
| *A61K 31/704* | (2006.01) | |
| *A61K 31/7068* | (2006.01) | |

(52) U.S. Cl.
CPC ...... *C07K 14/4726* (2013.01); *A61K 31/7064* (2013.01); *A61K 45/06* (2013.01); *A61P 35/02* (2018.01); *A61K 31/704* (2013.01); *A61K 31/7068* (2013.01); *A61K 38/00* (2013.01); *A61K 38/1732* (2013.01); *A61K 2300/00* (2013.01)

(58) Field of Classification Search
None
See application file for complete search history.

(56) References Cited

U.S. PATENT DOCUMENTS

| | | |
|---|---|---|
| 6,770,622 B2 | 8/2004 | Jarvis et al. |
| 9,272,014 B2 | 3/2016 | Chiriva-Internati et al. |
| 9,744,212 B2 | 8/2017 | Chiriva-Internati et al. |
| 2003/0054982 A1 | 3/2003 | Jarvis et al. |
| 2004/0023855 A1 | 2/2004 | John et al. |
| 2014/0243275 A1 | 8/2014 | Chiriva-Internati et al. |
| 2015/0157691 A1 | 6/2015 | Chiriva-Internati et al. |
| 2015/0157694 A1 | 6/2015 | Burton |
| 2015/0216931 A1 | 8/2015 | Chiriva-Internati et al. |

FOREIGN PATENT DOCUMENTS

| | | |
|---|---|---|
| WO | WO2012/135528 | 3/2013 |
| WO | WO 2013/151666 A2 | 10/2013 |
| WO | WO 2014/127275 A2 | 8/2014 |
| WO | WO 2015/052345 A1 | 4/2015 |
| WO | WO2015/085207 | 6/2015 |
| WO | WO2015/117127 | 8/2015 |
| WO | WO2017/160761 | 12/2017 |

OTHER PUBLICATIONS

Human Galectin-3 protein, UniProtKB Accession No. P17931, entered into UniProtKB/Swiss-Prot Nov. 1, 1990; accessed Nov. 25, 2019 at URL: uniprot.org/uniprot/ P17931, pp. 1-6 (Year: 1990).*
Ryan et al., "Regulation and function of the p53 tumor suppressor protein," Curr. Opin. Cell Biol. 13:332-337 (2001) (Year: 2001).*
Jorgensen et al., "Recent trends in stabilizing peptides and proteins in pharmaceutical formulation-considerations in the choice of excipients," Expert Opin. Drug Deliv. 6):1219-1230 (2009) (Year: 2009).*
Akahani, S. et al. "Galectin-3: A Novel Antiapoptic Molecule with a Functional BH1 (NWGR) Doman of Bcl-2 Family," Cancer Research, 1997, vol. 57, No. 23, pp. 5272-5276.
Bhagatji, P., et al. "Multiple cellular proteins modulate the dynamics of K-ras association with the plasma membrane," Biophysical Journal, 2010, vol. 99, No. 10, pp. 3327-3335.
Blanchard, H. et al. "Galectin-3 inhibitors: a patent review (2008-present)," Expert Opinion on Therapeutic Patents, 2014, vol. 24, No. 10, pp. 1053-1065.
De Falco, V., et al. "CD44 proteolysis increases CREB phosphorylation and sustains proliferation of thyroid cancer cells," Cancer Research, 2012, vol. 72, No. 6, pp. 1449-1458.
Ebrahim, A. H. et al. "Galectins in cancer: carcinogenesis, diagnosis, and therapy," Annals of Translational Medicine, 2014, vol. 2, No. 9, 7 pages.
Fermin Lee, A., et al. "Galectin-3 modulates Th17 responses by regulating dendritic cell cytokines," The American Journal Of Pathology, 2013, vol. 183, No. 4, pp. 1209-1222.
Funasaka, T., et al. "Nuclear transport of galectin-3 and its therapeutic implications," Seminars in Cancer Biology, 2014, vol. 27, pp. 30-38.

(Continued)

*Primary Examiner* — Julie Ha
*Assistant Examiner* — Kristina M Hellman
(74) *Attorney, Agent, or Firm* — Fenwick & West LLP; Kelly Harradine

(57) ABSTRACT

Compositions and methods for treating solid and hematological cancers, including Acute Myeloid Leukemia (AML), are provided herein. The methods include administering truncated, dominant-negative, forms of Galectin-3.

Figure 1:
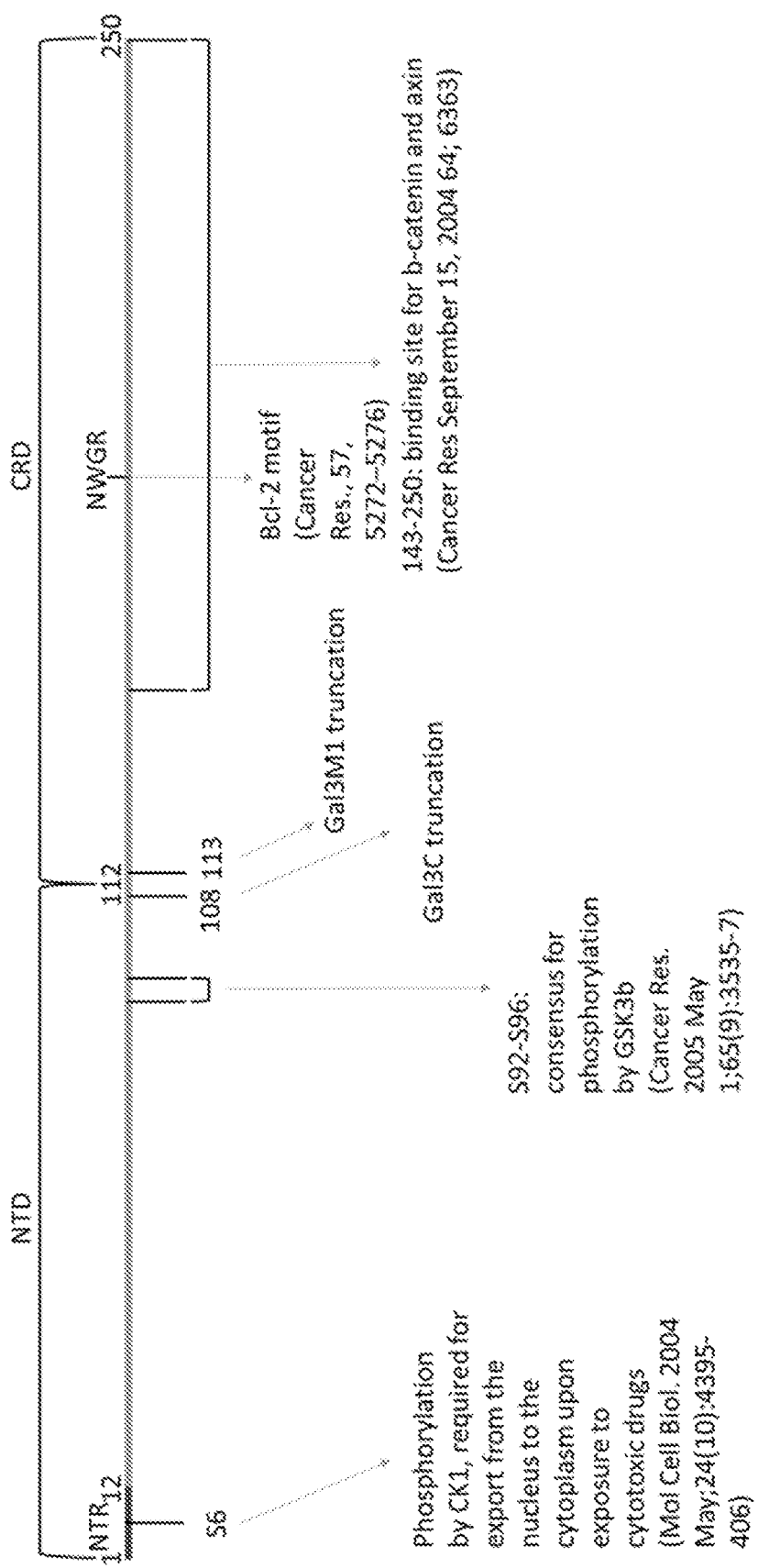

5 Claims, 8 Drawing Sheets
Specification includes a Sequence Listing.

(56) References Cited

OTHER PUBLICATIONS

Gupta-Rossi, N., et al. "Monoubiquitination and endocytosis direct gamma-secretase cleavage of activated Notch receptor," J Cell Biol, 2004, vol. 166, No. 1, pp. 73-83.

Jin, L., et al. "Targeting of CD44 eradicates human acute myeloid leukemic stem cells," Nature Medicine, 2006, vol. 12, No. 10, pp. 1167-1174.

Kuo, H. Y., et al. "Galectin-3 modulates the EGFR signalling-mediated regulation of Sox2 expression via c-Myc in lung cancer," Glycobiology, 2015, vol. 26, No. 2, pp. 155-165.

Liu, F. T. et al. "Galectins as modulators of tumour progression," Nature Reviews Cancer, 2005, vol. 5, No. 1, pp. 29-41.

Mirandola, L. et al. "Anti-Galectin-3 Therapy: A New Chance for Multiple Myeloma and Ovarian Cancer?" International Reviews of Immunology, 2014, vol. 33, No. 5, pp. 417-427.

Mirandola, L. et al. "Galectin-3 inhibition suppresses drug resistance, motility, invasion and angiogenic potential in ovarian cancer," Gynecologic Oncology, 2014, vol. 135, pp. 573-579.

Mirandola, L. et al. "Galectin-3C Inhibits Tumor Growth and Increases the Anticancer Activity of Bortezomib in a Murine Model of Human Multiple Myeloma," PloS one, 2011, vol. 6, No. 7, 14 pages.

Nakahara, S., et al. "Importin-mediated nuclear translocation of galectin-3," Journal of Biological Chemistry, 2006, vol. 281, No. 51, pp. 39649-39659.

Okamoto, I., et al. "Proteolytic release of CD44 intracellular domain and its role in the CD44 signaling pathway," J Cell Biol, 2001, vol. 155, No. 5, pp. 755-762.

Pelletier, L., et al. "Gamma-secretase-dependent proteolysis of CD44 promotes neoplastic transformation of rat fibroblastic cells," Cancer Research, 2006, vol. 66, No. 7, pp. 3681-3687.

Pena, C. et al. "Galectins as therapeutic targets for hematological malignancies: a hopeful sweetness," Annals of Translational Medicine, 2014, vol. 2, No. 9, 7 pages.

Qian, Y. et al. "Tumor suppression by p53: making cells senescent," Histology and Histopathology, 2010, vol. 25, No. 4, pp. 515-526.

Ruvolo, P. P. "Galectin 3 as a guardian of the tumor microenvironment," Biochima et Biophysica Acta (BBA)—Molecular Cell Research, 2015, vol. 1863, No. 3, pp. 427-437.

Shimura, T., et al. "Galectin-3, a novel binding partner of beta-catenin," Cancer Research, 2004, vol. 64, No. 18, pp. 6363-6367.

Shimura, T., et al. "Implication of galectin-3 in Wnt signaling," Cancer Research, 2005, vol. 65, No. 9, pp. 3535-3537.

Simon, M., et al. "Constitutive activation of the Wnt/beta-catenin signalling pathway in acute myeloid leukaemia," Oncogene, 2005, vol. 24, No. 14, pp. 2410-2420.

Song, S., et al. "Galectin-3 mediates nuclear beta-catenin accumulation and Wnt signaling in human colon cancer cells by regulation of glycogen synthase kinase-3beta activity." Cancer Research, 2009, vol. 69, No. 4, pp. 1343-1349.

Stanley, P. "Galectins CLIC cargo inside," Nature Cell Biology, 2015, vol. 16, No. 6, pp. 506-507.

Takenaka, Y., et al. "Nuclear export of phosphorylated galectin-3 regulates its antiapoptotic activity in response to chemotherapeutic drugs," Molecular and Cellular Biology, 2004, vol. 24, No. 10, pp. 4395-4406.

PCT International Search Report and Written Opinion, PCT/US2017/022168, dated Sep. 12, 2017, 18 Pages.

Song, S., et al., "Galectin-3 Mediates Nuclear β-Catenin Accumulation and Wnt Signaling in Human Colon Cancer Cells by Regulation of GSK-3β Activity," Cancer Res. Author Manuscript, Feb. 15, 2009, vol. 69, pp. 1-16.

Mirandola, L., et al., "Anti-Galectin-3 Therapy A New Chance For Multiple Myeloma and Ovarian Cancer?" International Reviews Of Immunology, 2014, vol. 33, pp. 417-427.

* cited by examiner

US 10,717,774 B2

COMPOSITIONS AND METHODS FOR TREATING CANCERS

1. RELATED APPLICATIONS

The present application claims priority to U.S. Provisional Patent Application Ser. No. 62/308,045 with a filing date of Mar. 14, 2016 and entitled: "COMPOSITIONS AND METHODS FOR TREATING CANCERS", the disclosure of which is herein incorporated by reference in its entirety.

SEQUENCE LISTING

The instant application contains a Sequence Listing which has been submitted electronically in ASCII format and is hereby incorporated by reference in its entirety. Said ASCII copy, created on Feb. 24, 2020, is named 36528US_CRF-_sequencelisting.txt and is 10,546 bytes in size.

2. BACKGROUND

Galectins are S-type lectins that bind β-galactose-containing glycoconjugates. Since the discovery of the first galectin in animal cells in 1975, fifteen mammalian galectins have been isolated and have been shown to be involved in diverse biological processes, such as cell adhesion, regulation of growth, and programmed cell death. Galectins have also been implicated in tumor development and progression, with Galectin-3 ("Gal-3") having been shown to be involved in cancer cell adhesion, metastasis, angiogenesis, invasion, growth, and resistance to chemotherapies. See Ebrahim et al., "Galectins in cancer: carcinogenesis, diagnosis and therapy," *Ann. Transl. Med.* 2(9):88 (2014).

Like other galectins, Gal-3 has a characteristic C-terminal carbohydrate recognition domain ("CRD"). Unlike other galectins, however, Galectin-3 also includes an amino-terminal domain that confers multivalent behavior. The amino-terminal domain allows Gal-3 to cross-link carbohydrate-containing ligands on cell surfaces and in the extracellular matrix, thereby modulating cell adhesion and signaling.

Alone, the C-terminal CRD of Gal-3 cannot cross-link carbohydrate-containing ligands on cell surfaces; without the N-terminal domain, the C-terminal CRD has no hemagglutination activity lacks the cooperative binding that characterize the intact lectin. Recombinantly expressed N-terminal truncations of Gal-3 protein that retain the C-terminal CRD but lack the amino-terminal multimerization domain have been demonstrated to act as dominant-negative inhibitors of Gal-3-mediated cross-linking, interfering with various tumor-associated properties in in vitro assays and inhibiting tumor growth and metastasis in animal models of various human cancers. Such N-terminal truncation proteins have thus been proposed for use in treating various human cancers.

For example, one such truncation, "Gal3C", has been proposed for treatment of breast cancer, prostate cancer, colon cancer, lung cancer, and all solid and hematological forms of cancer, alone or in combination with chemotherapy, see U.S. Pat. No. 6,770,622; for treatment of multiple myeloma in combination with proteasome inhibitors such as bortezomib and carfilzomib, see U.S. Pat. No. 9,272,014; and for treatment of ovarian cancer, alone or in combination with chemotherapeutic agents such as paclitaxel, carboplatin, or bortezomib, see U.S. pre-grant publication 2015/0157691. U.S. pre-grant publication 2015/0216931 describes a small genus of N-terminal Gal-3 truncation proteins, collectively termed "Gal3M", that contain one or more identified amino acid changes as compared to native human Gal-3. Recombinantly-expressed Gal3M proteins are predicted to be useful in treating solid tumors, including both carcinomas and sarcomas, and a wide range of hematological cancers, including B cell lymphoma, T cell lymphoma, NK cell lymphoma, Hodgkin's lymphoma, non-Hodgkin's lymphoma, acute myelocytic leukemia ("AML"), acute lymphocytic leukemia ("ALL"), chronic lymphocytic leukemia (CLL), chronic myelogenous leukemia ("CML"), and myelodysplastic syndrome, either alone or in combination with proteasome inhibitors such as bortezomib and carfilzomib and other chemotherapeutic agents.

Despite the therapeutic promise of dominant-negative N-terminal Gal-3 truncation proteins, further optimization of Gal-3 dominant negative truncation proteins is still required. And despite the promise of dominant-negative N-terminal Gal-3 truncation proteins as treatments for those cancers for which the animal model data are widely accepted as predictive of efficacy in specific cancers, see e.g., Mirandola et al., "Anti-Galectin-3 Therapy: A New Chance for Multiple Myeloma and Ovarian Cancer?", *Int. Rev. Immunol.*, 33:417-427 (2014); and Pena et al., "Galectins as therapeutic targets for hematological malignancies: a hopeful sweetness", *Ann. Transl. Med.* 2(9):87 (2014), the proposed extrapolation to additional cancers is predicated on a small number of galectin-3-mediated biological pathways that are thought to be shared by these additional cancers. There is, therefore, a need in the art to identify all cancers against which N-terminally truncated Gal-3 proteins will ultimately prove effective.

3. SUMMARY

In a first aspect, novel Galectin-3 N-terminal truncation proteins are provided.

In specific embodiments, the protein has the amino acid sequence of SEQ. ID NO. 5 (CBPI.001) or SEQ. ID NO. 7 (CBPI.002/Gal3M1).

In a variety of embodiments, the novel N-terminal Gal-3 truncation protein includes residues 108-250 of the native Gal-3 protein, further comprising one of the substitutions present in Gal3M1 (CBPI.002), two of the substitutions present in Gal3M1, three of the substitutions present in Gal3M1, or four of the substitutions present in Gal3M1, in any combination. In some embodiments, the novel N-terminal Gal-3 truncation protein includes residues 109-250 of the native Gal-3 protein, further comprising zero, one, two, three, or four of the substitutions present in Gal3M1 (CBPI.002), in any combination.

In some embodiments, the novel N-terminal Gal-3 truncation protein includes residues 110-250 of the native Gal-3 protein, further comprising zero, one, two, three or four of the substitutions present in Gal3M1 (CBPI.002), in any combination.

In some embodiments, the novel N-terminal Gal-3 truncation protein includes residues 111-250 of the native Gal-3 protein, further comprising zero, one, two, three or four of the substitutions present in Gal3M1 (CBPI.002), in any combination.

In some embodiments, the novel N-terminal Gal-3 truncation protein includes residues 112-250 of the native Gal-3 protein, further comprising zero, one, two, three or four of the substitutions present in Gal3M1 (CBPI.002), in any combination.

In some embodiments, the novel N-terminal Gal-3 truncation protein includes residues 113-250 of the native Gal-3 protein, further comprising zero, one, two, three or four of the substitutions present in Gal3M1 (CBPI.002), in any combination.

In yet other embodiments, the novel N-terminal Gal-3 truncation protein includes residues 114-250, 115-250, 116-260, 117-250, 118-250, 119-250, 120-250, 121-250, 122-250, 123-250, or 124-250, wherein each such embodiment optionally comprises one, two, three, or four of the substitutions present in Gal3M1 (CBPI.002), in any combination.

In various embodiments, the N-terminal truncation proteins include, or further include, substitutions at one or more of residues 113, 114, 118, and 248 as compared to the native Gal-3 protein that are different from those substitutions found in Gal3M1. In particular embodiments, the substitutions are conservative substitutions. In some embodiments, the substitutions are semi-conservative substitutions.

In some embodiments, the N-terminal truncation proteins include, or further include, substitutions at one or more of residues 113, 114, 118, and 248 as compared to the Gal3M1 protein. In particular embodiments, the substitutions are conservative substitutions. In some embodiments, the substitutions are semi-conservative substitutions.

In various embodiments, the N-terminal truncation proteins include, or further include, at least 1, 2, 3, 4, 5 or more substitutions as compared to native Gal-3 at residues other than 113, 114, 118 and 248. In certain embodiments, the N-terminal truncation proteins include, or further include, at least 6, 7, 8, 9, or 10 or more amino acid substitutions as compared to native Gal-3 at residues other than 113, 114, 118 and 248 (numbering according to native Gal-3). In certain embodiments, the substitutions are conservative substitutions. In some embodiments, the substitutions are semi-conservative substitutions.

In typical embodiments, the N-terminal truncation protein has 70% or more, 80% or more, 85% or more, 90% or more, or 95% or more sequence identity to native Gal-3 protein. In certain embodiments, the N-terminal truncation protein has 85%, 86%, 87%, 88%, 89%, or 90% sequence identity to Gal-3 native protein. In some embodiments, the N-terminal truncation protein has 91%, 92%, 93%, 94%, or 95% sequence identity to Gal-3 native protein. In some embodiments, the N-terminal truncation protein has 96%, 97%, 98%, 99%, or 100% sequence identity to Gal-3 native protein.

In another aspect, polynucleotides that encoding such proteins are provided, including nucleic acid vectors, including nucleic acid expression vectors, that comprise polynucleotides that encode the novel N-terminal truncation proteins.

In another aspect, methods for treating cancer are provided. The methods comprise administering to a subject having a cancer a therapeutically effective amount of the pharmaceutical composition comprising the novel Gal-3 N-terminal truncation protein.

In some embodiments, the amount is effective to reduce the activity in the cancer cells of at least one signal transduction pathway required for tumor growth or survival.

In particular embodiments, the signal transduction pathway is selected from the group consisting of: Ras, beta-catenin, Akt, extracellular signal-regulated kinase (ERK), c-Jun N-terminal kinase (JNK), and CD44 signaling pathways.

In certain embodiments, the signal transduction pathway is the beta-catenin signal transduction pathway. In some embodiments, the signal transduction pathway is the CD44 signaling pathway.

In a variety of embodiments, the cancer is a hematological malignancy. In some embodiments, the hematological malignancy is selected from the group consisting of: T-cell acute lymphocytic leukemia, T-cell acute lymphoblastic leukemia, T-cell chronic lymphocytic leukemia, non-Hodgkin lymphomas, Hodgkin lymphoma, multiple myeloma, plasma cell leukemia, B-cell acute lymphocytic leukemia, B-cell acute lymphoblastic leukemia, chronic myelogenous leukemia, and acute myeloid leukemia (AML).

In particular embodiments, the hematological malignancy is AML. In certain embodiments, the Gal-3 N-terminal truncation protein is administered in combination with the pharmaceutical composition of claim 4 at least one AML induction chemotherapeutic agent. The induction chemotherapeutic agent, in select embodiments, is idarubicin. The induction chemotherapeutic agent in certain embodiments is cytarabine.

In some embodiments, the cancer is a solid malignancy. In particular embodiments, the cancer is selected from the group consisting of: breast cancer, triple-negative breast cancer, non-small cell lung cancer, small-cell lung cancer, esophageal cancer, gastric cancer, hepatocellular carcinoma, pancreatic cancer, brain tumors, melanomas, skin cancer, prostate cancer, ovarian cancer, cervical cancer, colorectal cancer, and renal-cell carcinoma. In a subset of these embodiments, the Gal-3 N-terminal truncation protein is administered in combination with at least one antineoplastic chemotherapeutic or biological agent. In particular embodiments, the at least one additional agent is selected from the group consisting of boron compounds, alkylating agents, antimetabolites, anthracyclines, topoisomerase inhibitors, mitotic inhibitors, and corticosteroids.

In another aspect, methods of treating cancer with the Gal-3 N-terminal truncation protein, Gal3C, are provided. The methods comprise administering a therapeutically effective amount of a protein having the amino acid sequence of SEQ ID NO:3, wherein the amount is effective to reduce the activity in the cancer cells of at least one signal transduction pathway required for tumor growth or survival, wherein the pathway is selected from the group consisting of Ras, beta-catenin, Akt, extracellular signal-regulated kinase (ERK), c-Jun N-terminal kinase (JNK), and CD44 signaling pathways, and wherein the cancer is not multiple myeloma or ovarian cancer.

4. BRIEF DESCRIPTION OF THE DRAWINGS

This patent or patent application file consists of at least one drawing executed in color. Copies of this patent or patent application with color drawing(s) will be provided by the Office upon request and payment of the required fee.

FIG. 1—provides a schematic representation of the domain structure of native Galectin-3, Gal3C, and Gal3M1.

Figure 2:
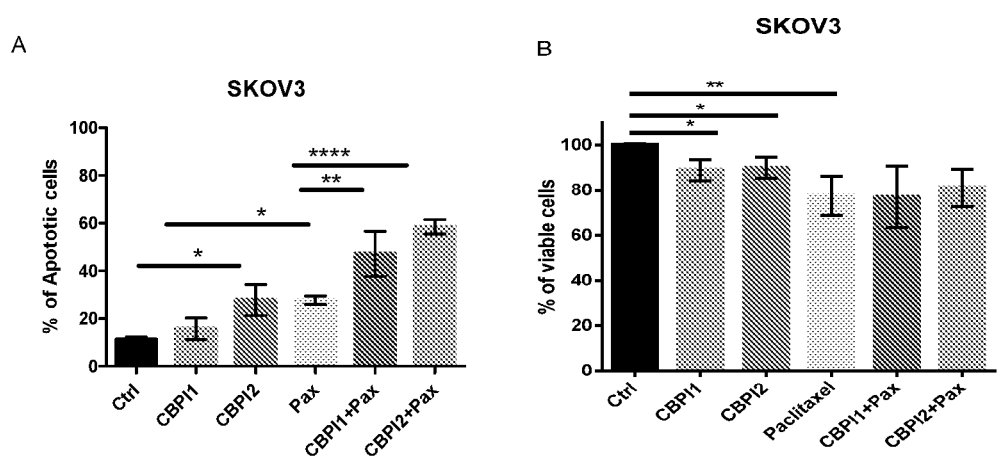

FIG. 2—results from MTT analysis schematically illustrate the effect of CBPI1 and CBPI2 in ovarian cancer. Panel A) shows that both CBPI1 and CBPI2 combined treatment with Paclitaxel (Pax) significantly increase the rate of apoptosis in SKOV3 cells, as compared with Pax, alone. Panel B) shows that CBPI1 and CBPI2 alone significantly decrease cell viability of metabolically-active cells, as compared to the control cells.

Figure 3:
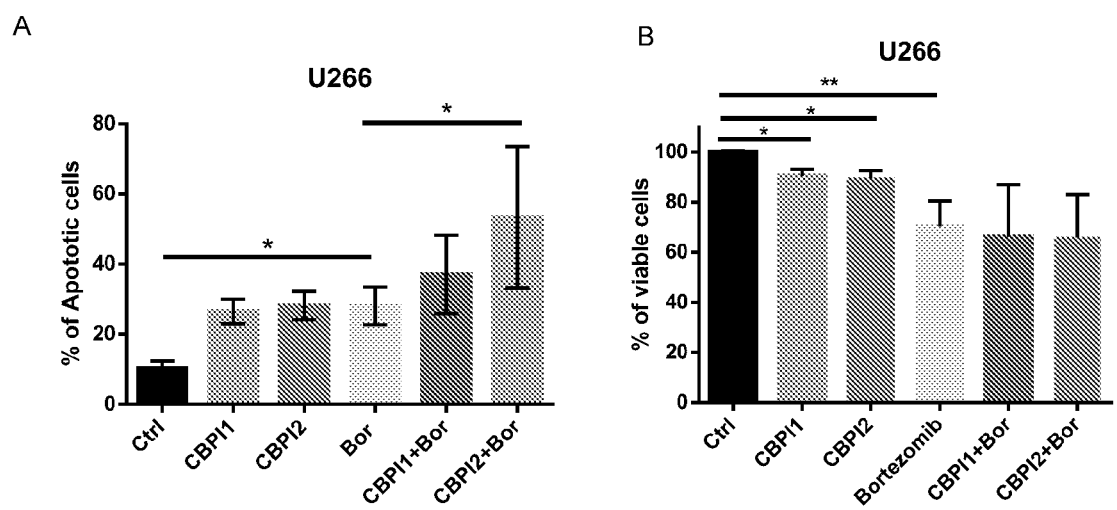

FIG. 3—results from MTT analysis schematically illustrate the effect of CBPI1 and CBPI2 in multiple myeloma. Panel A) shows that CBPI2 combined treatment with Bortezomib (Bor) significantly increase the rate of apoptosis of U266 cells, as compared with Bor, alone. Panel B) shows that CBPI1 and CBPI2 alone, significantly decrease the viability of metabolically-active cells.

Figure 4:
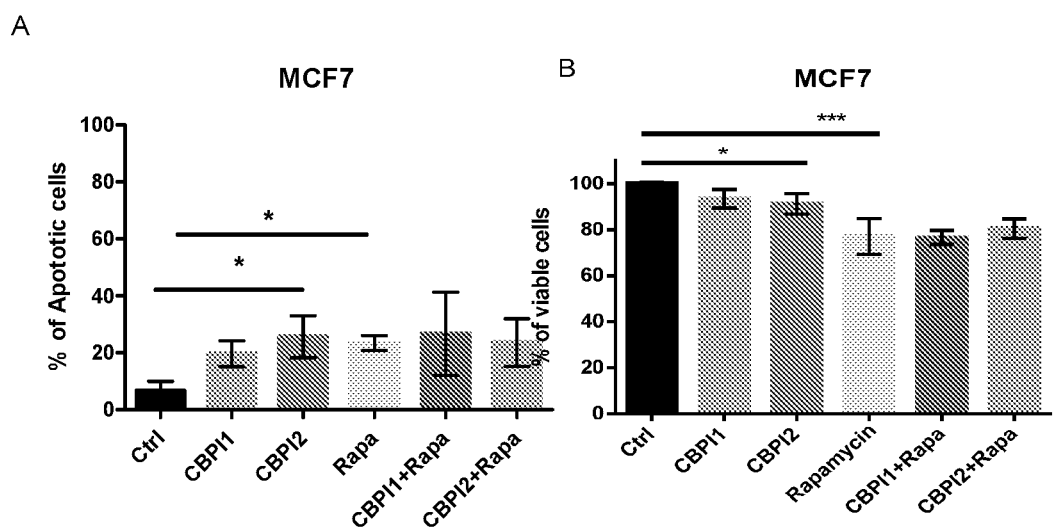

FIG. 4—results from MTT analysis schematically illustrate the effects of CBPI1 and CBPI2 in breast cancer. Panel A) shows that CBPI2 alone, significantly increases the apoptotic rate of MCF7 cells, as compared to control cells. Panel B) shows that CBPI2 alone, significantly decreases the viability of metabolically-active cells.

Figure 5:
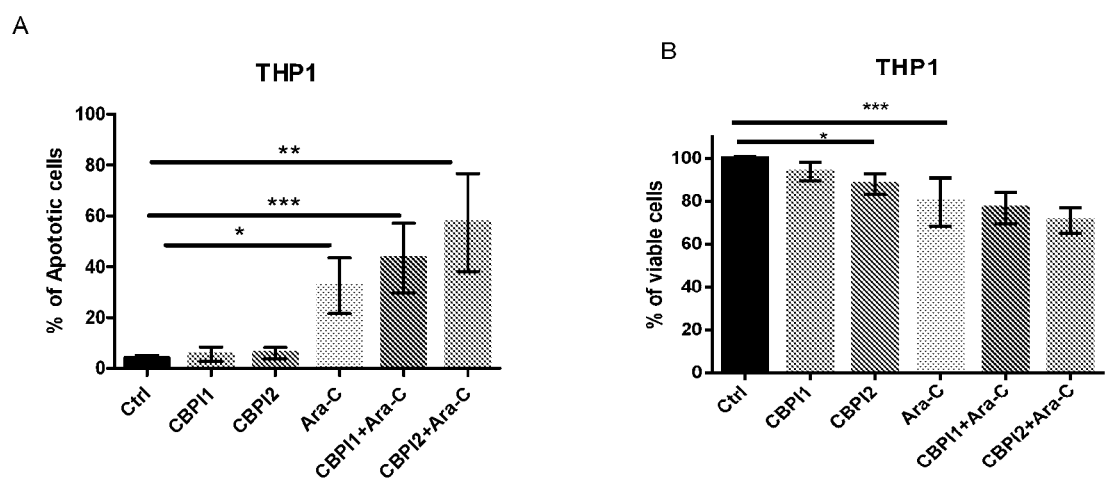

FIG. 5—results from MTT analysis schematically illustrate the effects of CBPI1 and CBPI2 in acute monocytic leukemia. Panel A) shows that CBPI1 and CBPI2, in combination with Ara-C, significantly increase the apoptosis rate of THP1 cells, as compared to control cells. Panel B) shows that CBPI2 alone significantly decreases the viability of metabolically-active cells.

Figure 6A:
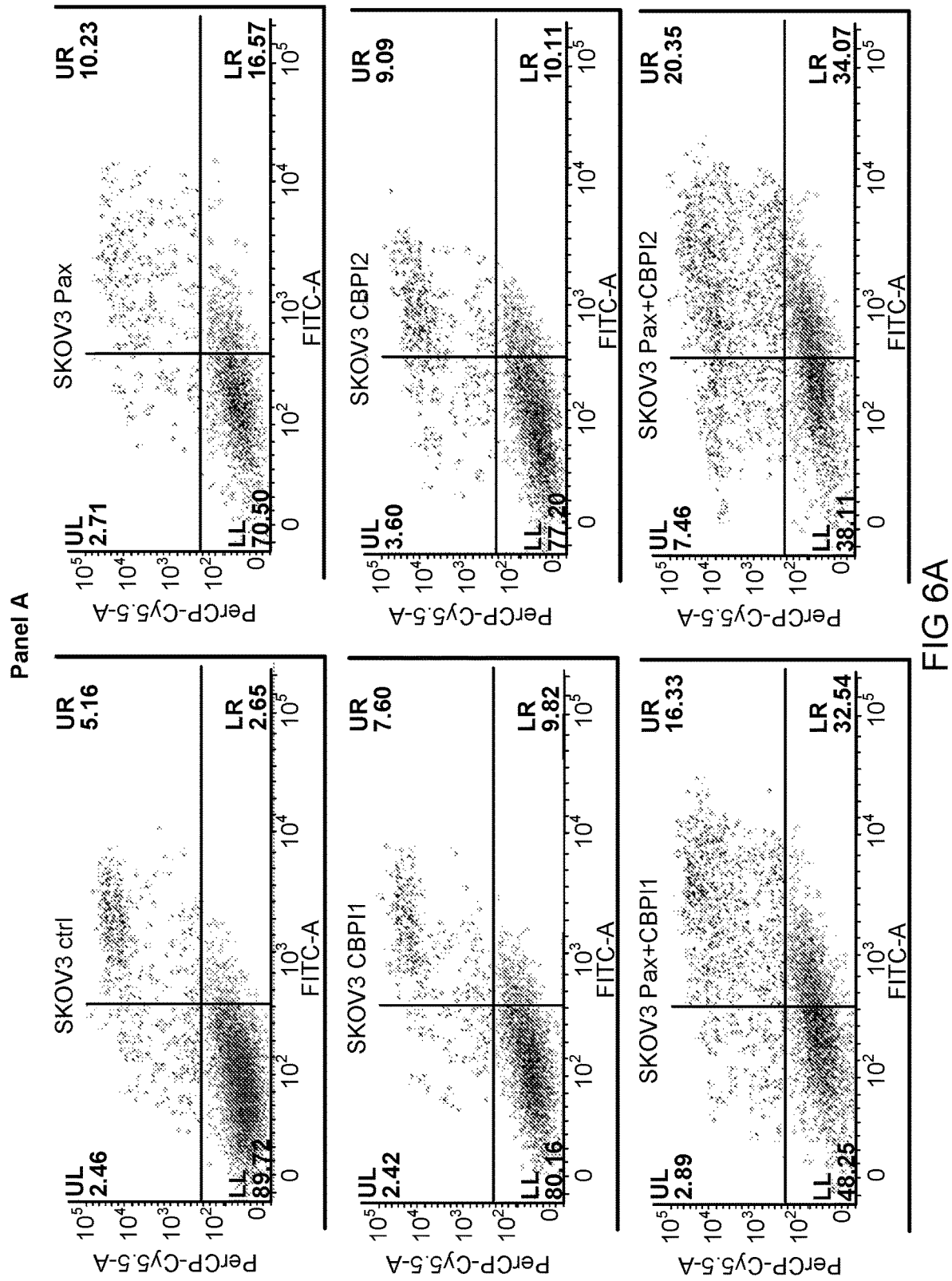
Figure 6B:
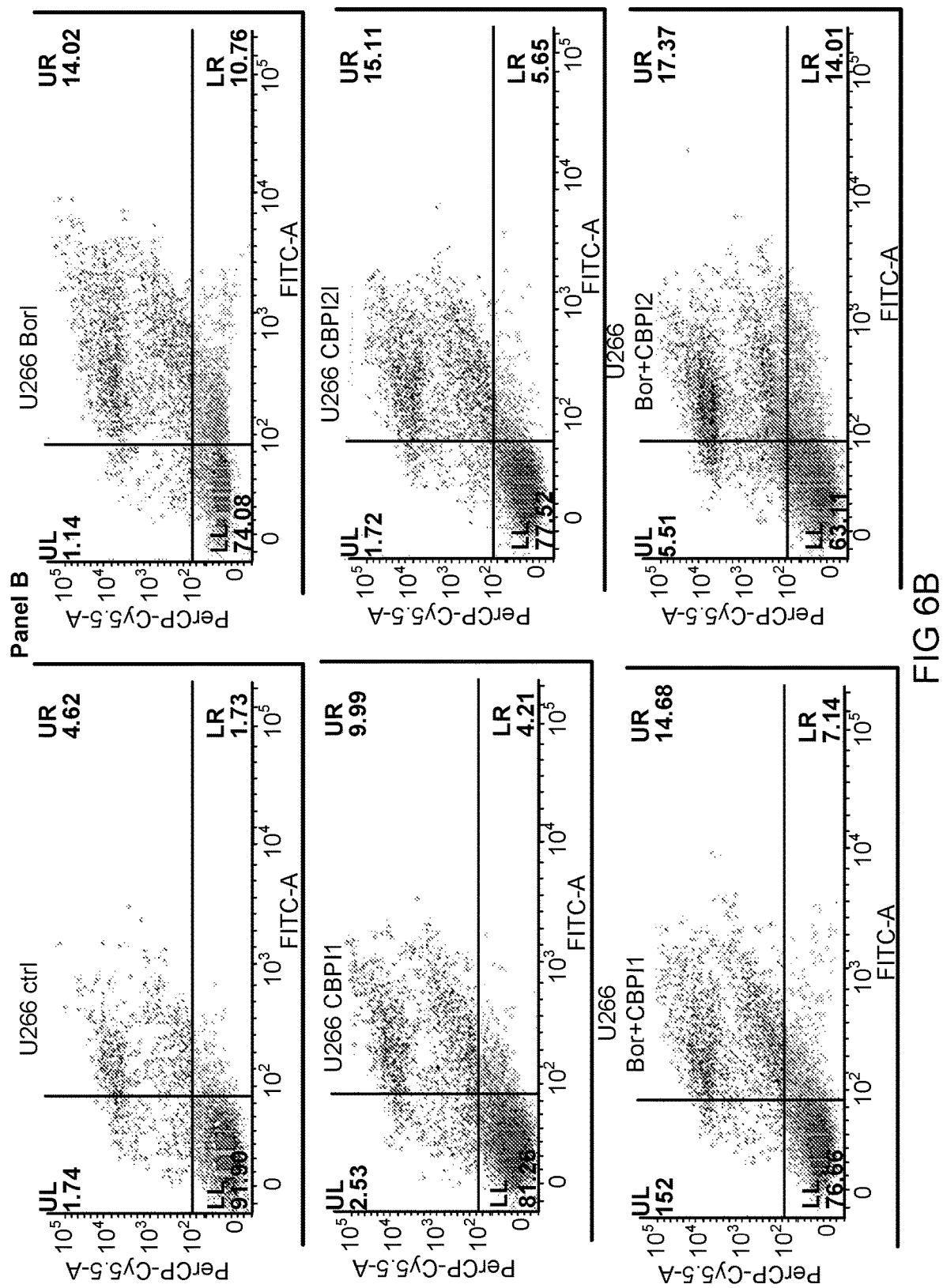
Figure 6C:
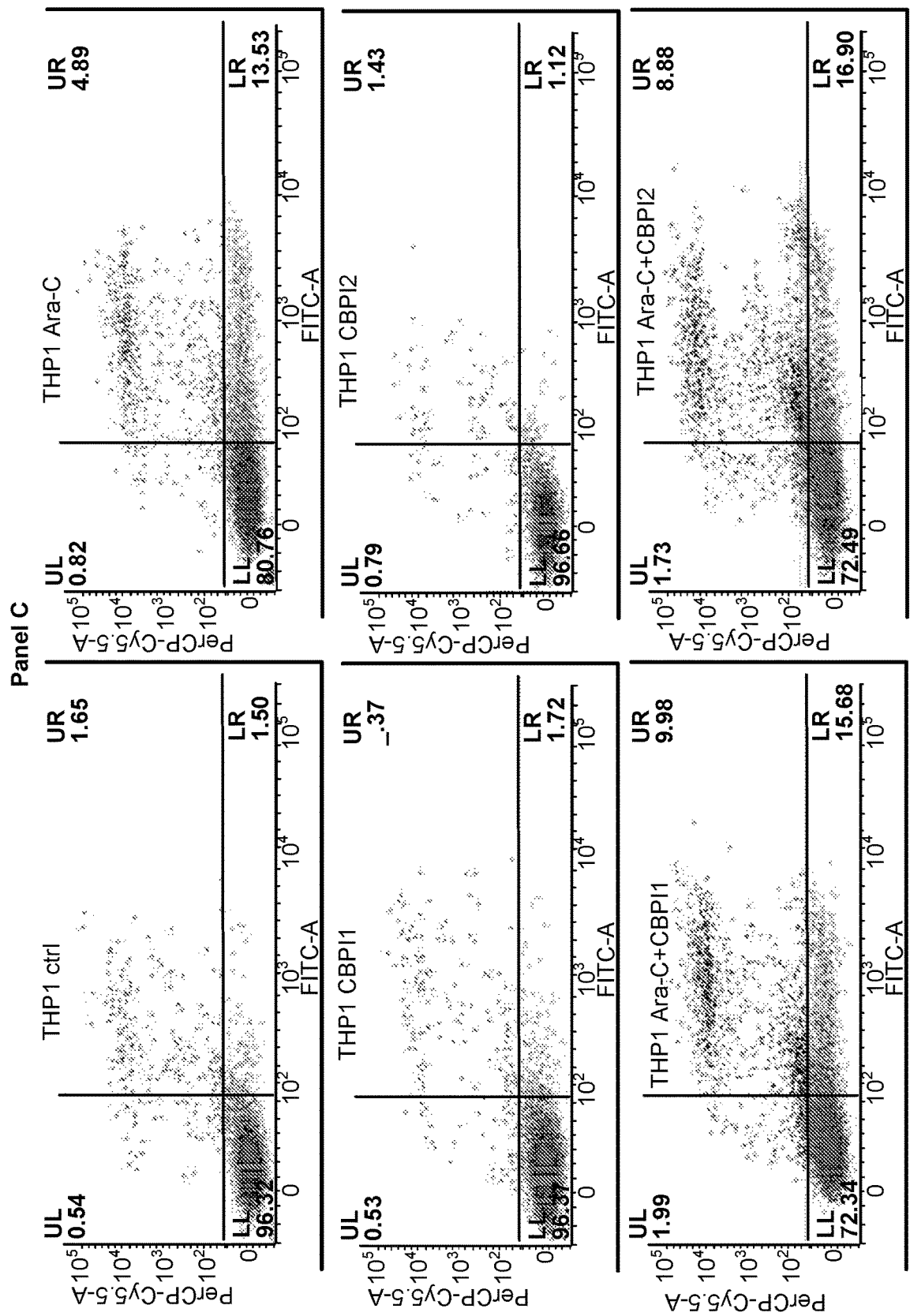

FIG. 6—illustrates dot plots representative of the results of the apoptosis analysis for each cell line analyzed herein: Panel A) SKOV3; Panel B) U266; Panel C) THP1.

5. DETAILED DESCRIPTION

5.1. Definitions

Terms used in the claims and specification are defined as set forth below unless otherwise specified.

The term "amino acid" refers to natural amino acids, unnatural amino acids, and amino acid analogs, all in their D and L stereoisomers, unless otherwise indicated, if their structures allow such stereoisomeric forms.

Natural amino acids are alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-a 5 aminobutyric acid, 6-aminocaproic acid, 2-aminoheptanoic acid, 2-aminoisobutyric acid, 3-aminoisobutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methyl alanine ("MeAla" or "Nime"), Nalkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain functional group has been chemically blocked, reversibly or irreversibly, or otherwise modified to another functional group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone. As used herein, the term "peptide" refers a short polymer of amino acids linked together by peptide bonds. In contrast to other amino acid polymers (e.g., proteins, polypeptides, etc.), peptides are of about 50 amino acids or less in length. A peptide may comprise natural amino acids, non-natural amino acids, amino acid analogs, and/or modified amino acids. A peptide may be a subsequence of naturally occurring protein or a non-natural (synthetic) sequence.

As used herein, a "conservative amino acid substitution" refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

As used herein, a "semi-conservative amino acid substitution" refers to the substitution of an amino acid in a peptide or polypeptide with another amino acid within the same class. Naturally occurring residues may be divided into classes based on common side chain properties, for example: polar positive (histidine (H), lysine (K), and arginine (R)); polar negative (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine.

In some embodiments, unless otherwise specified, a conservative or semiconservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs. Non-conservative substitutions may involve the exchange of a member of one class for a member from another class.

"Non-conservative amino acid substitutions" may involve the exchange of a member of one class for a member from another class.

The term "protein" is used herein regardless of length, and is used synonymously with the term "polypeptide."

The terms "peptide mimetic" or "peptidomimetic" refer to a peptide-like molecule that emulates a sequence derived from a protein or peptide. A peptide mimetic or peptidomimetic may contain amino acids and/or non-amino acid components. Examples of peptidomimetics include chemically modified peptides, peptoids (side chains are appended to the nitrogen atom of the peptide backbone, rather than to the α-carbons), β-peptides (amino group bonded to the β carbon rather than the α carbon), etc.

The terms "administration of" or "administering" a therapeutic compound or a composition refer to introducing the compound or composition into the body of a subject in need of treatment. The term includes directly introducing the compound or composition into the subject's body, such as by parenteral administration, or indirectly introducing the compound or composition, for example by prescribing that the compound or composition be introduced into the subject's body, by ordering that the compound or composition be introduced into the subject's body, or by providing the compound or composition for use by the subject in accordance with instructions or advice. Administration of or administering includes administration by any route of administration, including: oral administration; buccal administration; sublingual administration; parenteral administration, including intravenous, intramuscular, subcutaneous, intraperitoneal, intrathecal, and intracerebroventricular administration; intratumoral administration; nasal administration; pulmonary administration; rectal administration.

As used herein, a "subject" broadly refers to any animal, including but not limited to, human and non-human animals. In typical embodiments, the subject is a mammal, including a human. The term "human" includes human subjects of either sex and at any stage of development (e.g., fetuses, neonates, infants, juveniles, adolescents, adults). As used herein, the term "patient" refers to a human subject who is being treated for a disease or condition.

The term "effective amount" refers to the amount of the subject compound or composition sufficient to elicit a desired biological response in a cell, tissue, or organism.

The term "therapeutically effective amount" refers to the amount of the subject compound or composition sufficient to provide a therapeutic or clinical benefit to the subject. The therapeutic or clinical benefit may include alleviation of symptoms, reduction in the severity of the disease, slowing disease progression, stopping disease progression, increasing overall survival, increasing progression-free survival, increasing efficacy of other therapies.

An effective amount or therapeutically effective amount can be administered in one or more administrations, applications or dosages and is not intended to be limited to a particular formulation or administration route.

As used herein, the terms "treatment" or "treating" means obtaining a beneficial or intended clinical result. The beneficial or intended clinical result may include alleviation of symptoms, reduction in the severity of the disease, slowing disease progression, stopping disease progression, increasing overall survival, increasing progression-free survival, increasing efficacy of other therapies.

As used herein, a "pharmaceutically acceptable" component is one that is suitable for use with subjects, e.g., humans and/or animals, without undue adverse side effects (such as toxicity, irritation, and allergic response) commensurate with a clinical benefit/risk ratio.

As used herein, the terms "resistant" or "refractory" when referring to a cancer mean that the cancer cells are no longer responsive to a prior chemotherapeutic or other treatment regimen, such as radiation therapy. The terms "sensitize" or "resensitize" when referring to a cancer means that the cancer cells again become responsive to a prior chemotherapeutic or other treatment regimen, such as radiation therapy, to which they had become resistant or refractory.

As used herein, the term "sequence identity" with respect to peptides and polypeptides refers to the degree to which two peptide or polypeptide sequences have the same sequential composition of monomer subunits. The "percent sequence identity" is calculated by: (1) comparing two optimally aligned sequences over the length of the shorter sequence; (2) determining the number of positions containing identical amino acids to yield the number of matched positions, (3) dividing the number of matched positions by the total number of positions in the shorter sequence, and (4) multiplying the result by 100 to yield the percent sequence identity.

The term "sequence similarity" refers to the degree with which two peptide or polypeptide sequences differ only by conservative and/or semi-conservative amino acid substitutions, as context dictates. The "percent sequence similarity" is calculated by: (1) comparing two optimally aligned sequences over the length of the shorter sequence; (2) determining the number of positions containing (i) identical monomers and (ii) conservative and/or semi-conservative substitutions, as context dictates, to yield the number of "similar" positions; (3) dividing the number of similar positions by the total number of positions in the shorter sequence; and (4) multiplying the result by 100 to yield the percent sequence identity or percent sequence similarity.

5.2. Further Interpretational Conventions

Unless explicitly defined otherwise, all technical and scientific terms used herein have the same meaning as commonly understood by one of ordinary skill in the art to which this invention pertains.

Whenever an amino acid position is identified by number, that number refers to the position in the native human Gal-3 protein.

As used herein and in the appended claims, the singular forms "a", "an", and "the" include plural referents unless the context clearly dictates otherwise.

Where a range of values is provided, unless explicitly stated otherwise the range includes the recited endpoints. It is to be further understood that each intervening value between lower and upper limit of the range is also specifically disclosed, with those intervening values to the tenth of the unit of the lower limit unless the context clearly dictates otherwise. Where the stated range includes one or both of the limits, ranges excluding either or both of those included limits are also included in the invention.

The publications discussed herein are provided solely for their disclosure prior to the filing date of the present application, and are incorporated herein by reference to disclose and describe the methods and/or materials in connection with which the publications are respectively cited. It is to be understood that the present disclosure supersedes any disclosure of an incorporated publication to the extent there is a contradiction; in particular, to the extent such publications set out definitions of a term that conflict with the explicit or implicit definition of the present disclosure, the definition of the present disclosure controls.

It is to be understood that this invention is not limited to particular embodiments described. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible, unless otherwise stated.

It is also to be understood that the terminology used herein is for the purpose of describing particular embodiments only, and is not intended to be limiting, since the scope of the present invention will be limited only by the appended claims.

5.3. Dominant Negative Gal-3 N-Terminal Truncation Proteins

In a first aspect, novel dominant negative galectin-3 N-terminal truncation proteins are provided.

5.3.1. Native Human Gal-3 Protein

Human Gal-3 is encoded by a single gene, LGALS3, located on chromosome 14, locus q21-q22. The LGALS3 gene encodes a 250 amino acid protein having the following amino acid sequence (GenBank accession no. CAG33178.1):

```
                                                    (SEQ ID NO.: 1)
  1   MADNFSLHDA LSGSGNPNPQ GWPGAWGNQP AGAGGYPGAS YPGAYPGQAP

51   PGAYPGQAPP GAYPGAPGAY PGAPAPGVYP GPPSGPGAYP SSGQPSATGA

101   YPATGPYGAP AGPLIVPYNL PLPGGVVPRM LITILGTVKP NANRIALDFQ

151   RGNDVAFHFN PRFNENNRRV IVCNTKLDNN WGREERQSVF PFESGKPFKI

201   QVLVEPDHFK VAVNDAHLLQ YNHRVKKLNE ISKLGISGDI DLTSASYTMI
```

The full length 750 nt cDNA sequence (without stop codon) has the following sequence (GenBank accession no. CR542097.1):

```
                                                    (SEQ ID NO.: 2)
  1   ATGGCAGACA ATTTTTCGCT CCATGATGCG TTATCTGGGT CTGGAAACCC

51   AAACCCTCAA GGATGGCCTG GCGCATGGGG GAACCAGCCT GCTGGGGCAG

101   GGGGCTACCC AGGGGCTTCC TATCCTGGGG CCTACCCCGG GCAGGCACCC

151   CCAGGGGCTT ATCCTGGACA GGCACCTCCA GGCGCCTACC CTGGAGCACC

201   TGGAGCTTAT CCCGGAGCAC CTGCACCTGG AGTCTACCCA GGGCCACCCA

251   GCGGCCCTGG GGCCTACCCA TCTTCTGGAC AGCCAAGTGC CCCCGGAGCC

301   TACCCTGCCA CTGGCCCCTA TGGCGCCCCT GCTGGGCCAC TGATTGTGCC

351   TTATAACCTG CCTTTGCCTG GGGGAGTGGT GCCTCGCATG CTGATAACAA

401   TTCTGGGCAC GGTGAAGCCC AATGCAAACA GAATTGCTTT AGATTTCCAA

451   AGAGGGAATG ATGTTGCCTT CCACTTTAAC CCACGCTTCA ATGAGAACAA

501   CAGGAGAGTC ATTGTTTGCA ATACAAAGCT GGATAATAAC TGGGGAAGGG

551   AAGAAAGACA GTCGGTTTTC CCATTTGAAA GTGGGAAACC ATTCAAAATA

601   CAAGTACTGG TTGAACCTGA CCACTTCAAG GTTGCAGTGA ATGATGCTCA

651   CTTGTTGCAG TACAATCATC GGGTTAAAAA ACTCAATGAA ATCAGCAAAC

701   TGGGAATTTC TGGTGACATA GACCTCACCA GTGCTTCATA TACATGATA
```

The basic domain structure of the human Gal-3 protein is shown in FIG. 1. The N-terminal domain ("NTD") mediates multimerization and extends approximately from amino acid 1 to residue 112. The C-terminal carbohydrate binding domain ("CRD") extends approximately from amino acid 112 through residue 250. Various other functional features are also indicated. The serine at position 6 ("S6"), which is subject to phosphorylation by CK1, is required for export from the nucleus to the cytoplasm upon exposure of cells to cytotoxic drugs (Takenaka et al., *Mol. Cell. Biol.* 24(10): 4395-4406 (2004)). The sequence from Serine 92 to Serine 96 ("S92-S96") is a consensus sequence for phosphorylation by GSK3b (Shimura et al., *Cancer Res.* 65(9):3535-3537 (2005)). The four amino acid sequence NWGR (SEQ ID NO: 9) in the carbohydrate domain ("NWGR" (SEQ ID NO: (9):3535-3537 (2005)). The four amino acid sequence NWGR in the carbohydrate domain ("NWGR") is a Bcl-1 motif *(Cancer Res.* 57:5272-5276 (Akahani et al., Cancer Res. 57:5272-5276 (1997)). The region from amino acids 143-250 is a binding site for β-catenin and axin (Shimura et al., *Cancer Res.* 64:6363-6367 (2004)).

5.3.2 Gal3C protein truncation Truncation Proteins

The N-terminal Gal-3 truncation protein, Gal3C, which has previously been shown to have anti-cancer efficacy in vitro and in animal models of various human cancers, is a 143 amino acid protein, beginning at residue 108 of the native Gal-3 protein, and has the following amino acid sequence:

```
                                               (SEQ ID NO: 3)
  1  GAPAGPLIVP YNLPLPGGVV PRMLITILGT VKPNANRIAL DFQRGNDVAF

51  HFNPRFNENN RRVIVCNTKL DNNWGREERQ SVFPFESGKP FKIQVLVEPD

101  HFKVAVNDAH LLQYNHRVKK LNEISKLGIS GDIDLTSASY TMI.
```

Except for deletion of amino acids 1-107, the sequence of Gal3C is identical to native human Gal-3, with 100% sequence identity to human Gal-3 amino acids 108-250.

In prior work, the Gal3C truncation protein was expressed from the following nucleic acid sequence:

```
                                               (SEQ ID NO: 4)
  1  GGCGCGCCGG CGGGCCCGCT GATTGTGCCG TATAACCTGC CGCTGCCGGG

51  CGGCGTGGTG CCGCGCATGC TGATTACCAT TCTGGGCACC GTGAAACCGA

101  ACGCGAACCG CATTGCGCTG GATTTTCAGC GCGGCAACGA TGTGGCGTTT

151  CATTTTAACC CGCGCTTTAA CGAAAACAAC CGCCGCGTGA TTGTGTGCAA

201  CACCAAACTG GATAACAACT GGGGCCGCGA AGAACGCCAG AGCGTGTTTC

251  CGTTTGAAAG CGGCAAACCG TTTAAAATTC AGGTGCTGGT GGAACCGGAT

301  CATTTTAAAG TGGCGGTGAA CGATGCGCAT CTGCTGCAGT ATAACCATCG

351  CGTGAAAAAA CTGAACGAAA TTAGCAAACT GGGCATTAGC GGCGATATTG

401  ATCTGACCAG CGCGAGCTAT ACCATGATTG CGCGCCGGC GGGCCCGCTG

451  ATTGTGCCGT ATAACCTGCC GCTGCCGGGC GGCGTGGTGC CGCGCATGCT

501  GATTACCATT CTGGGCACCG TGAAACCGAA CGCGAACCGC ATTGCGCTGG

551  ATTTTCAGCG CGGCAACGAT GTGGCGTTTC ATTTTAACCC GCGCTTTAAC

601  GAAAACAACC GCCGCGTGAT TGTGTGCAAC ACCAAACTGG ATAACAACTG

651  GGGCCGCGAA GAACGCCAGA GCGTGTTTCC GTTTGAAAGC GGCAAACCGT
```

```
701  TTAAAATTCA GGTGCTGGTG GAACCGGATC ATTTTAAAGT GGCGGTGAAC

751  GATGCGCATC TGCTGCAGTA TAACCATCGC GTGAAAAAAC TGAACGAAAT

801  TAGCAAACTG GGCATTAGCG GCGATATTGA TCTGACCAGC GCGAGCTATA

851  CCATGATT.
```

5.3.3. Novel N-Terminal Truncation Proteins

In a first embodiment, a novel Gal-3 N-terminal truncation protein, termed "CBPI.001", is provided. The CBPI.001 protein has the following amino acid sequence:

```
                                              (SEQ ID NO.: 5)
  1  APAGPLIVPY NLPLPGGVVP RMLITILGTV KPNANRIALD FQRGNDVAFH

51  FNPRFNENNR RVIVCNTKLD NNWGREERQS VFPFESGKPF KIQVLVEPDH

101  FKVAVNDAHL LQYNHRVKKL NEISKLGISG DIDLTSASYT MI.
```

CBPI.001 is identical in sequence to native Gal-3 amino acids 109-250.

In some embodiments, CBPI.001 is expressed from the following nucleic acid sequence.

```
                                              (SEQ ID NO: 6)
  1  GCGCCGGCGG GCCCGCTGAT TGTGCCGTAT AACCTGCCGC TGCCGGGCGG

51  CGTGGTGCCG CGCATGCTGA TTACCATTCT GGGCACCGTG AAACCGAACG

101  CGAACCGCAT TGCGCTGGAT TTTCAGCGCG GCAACGATGT GGCGTTTCAT

151  TTTAACCCGC GCTTTAACGA AAACAACCGC CGCGTGATTG TGTGCAACAC

201  CAAACTGGAT AACAACTGGG GCCGCGAAGA ACGCCAGAGC GTGTTTCCGT

251  TTGAAAGCGG CAAACCGTTT AAAATTCAGG TGCTGGTGGA ACCGGATCAT

301  TTTAAAGTGG CGGTGAACGA TGCGCATCTG CTGCAGTATA ACCATCGCGT

351  GAAAAAACTG AACGAAATTA GCAAACTGGG CATTAGCGGC GATATTGATC

401  TGACCAGCGC GAGCTATACC ATGATT.
```

In another embodiment, a novel Gal-3 N-terminal truncation protein, termed "Gal3M1" or "CBPI.002", is provided. The Gal-3M1 protein has the following amino acid sequence:

```
                                              (SEQ ID NO. 7)
  1  AVIVPNNLPL PGGVVPRMLI TILGTVKPNA NRIALDFQRG NDVAFHFNPR

51  FNENNRRVIV CNTKLDNNWG REERQSVFPF ESGKPFKIQV LVEPDHFKVA

101  VNDAHLLQYN HRVKKLNEIS KLGISGDIDL TSASYNMI.
```

The Gal-3M1 protein deletes amino acids 1-112 of the native Gal-3 protein, and includes 4 amino acid substitutions as compared to native Gal-3 amino acids 113-250, including substitutions at the first two amino acids of the Gal3M1 protein (amino acids 113 and 114 of the native protein). The alignment of Gal3M1 (CBPI.002) to native Gal-3 is shown below, with amino acid substitutions underlined.

```
Gal-3    1    MADNFSLHDA LSGSGNPNPQ GWPGAWGNQP AGAGGYPGAS    40
Gal3M1        ---------- ---------- ---------- ----------
```

-continued

```
Gal-3     41   YPGAYPGQAP PGAYPGQAPP GAYPGAPGAY PGAPAPGVYP    80
Gal3M1         ---------- ---------- ---------- ----------

Gal-3     81   GPPSGPGAYP SSGQPSATGA YPATGPYGAP AGPLIVPYNL   120
Gal3M1         ---------- ---------- ---------- --AVIVPNNL     8

Gal-3    121   PLPGGVVPRM LITILGTVKP NANRIALDFQ RGNDVAFHFN   160
Gal3M1     9   PLPGGVVPRM LITILGTVKP NANRIALDFQ RGNDVAFHFN    48

Gal-3    161   PRFNENNRRV IVCNTKLDNN WGREERQSVF PFESGKPFKI   200
Gal3M1    49   PRFNENNRRV IVCNTKLDNN WGREERQSVF PFESGKPFKI    88

Gal-3    201   QVLVEPDHFK VAVNDAHLLQ YNHRVKKLNE ISKLGISGDI   240
Gal3M1    49   QVLVEPDHFK VAVNDAHLLQ YNHRVKKLNE ISKLGISGDI   128

Gal-3    241   DLTSASYTMI  (SEQ ID NO: 1)                    250
Gal3M1         DLTSASYNMI  (SEQ ID NO: 7)                    138
```

Using the native residue numbering, the substitutions are P113A, L114V, Y118N, and T248N.

In some embodiments, the Gal-3M1 (CBPI.002) protein is expressed from the following nucleic acid sequence:

```
                                                  (SEQ ID NO: 8)
  1  GCGGTGATTG TGCCGAACAA CCTGCCGCTG CCGGGCGGCG TGGTGCCGCG

51  CATGCTGATT ACCATTCTGG GCACCGTGAA ACCGAACGCG AACCGCATTG

101  CGCTGGATTT TCAGCGCGGC AACGATGTGG CGTTTCATTT TAACCCGCGC

151  TTTAACGAAA ACAACCGCCG CGTGATTGTG TGCAACACCA AACTGGATAA

201  CAACTGGGGC CGCGAAGAAC GCCAGAGCGT GTTTCCGTTT GAAAGCGGCA

251  AACCGTTTAA AATTCAGGTG CTGGTGGAAC CGGATCATTT TAAAGTGGCG

301  GTGAACGATG CGCATCTGCT GCAGTATAAC CATCGCGTGA AAAAACTGAA

351  CGAAATTAGC AAACTGGGCA TTAGCGGCGA TATTGATCTG ACCAGCGCGA

401  GCTATAACAT GATT.
```

In some embodiments, the novel N-terminal Gal-3 truncation protein includes residues 108-250 of the native Gal-3 protein, further comprising one of the substitutions present in Gal3M1 (CBPI.002), two of the substitutions present in Gal3M1, three of the substitutions present in Gal3M1, or four of the substitutions present in Gal3M1, in any combination.

In some embodiments, the novel N-terminal Gal-3 truncation protein includes residues 109-250 of the native Gal-3 protein, further comprising zero, one, two, three, or four of the substitutions present in Gal3M1 (CBPI.002), in any combination.

In some embodiments, the novel N-terminal Gal-3 truncation protein includes residues 110-250 of the native Gal-3 protein, further comprising zero, one, two, three or four of the substitutions present in Gal3M1 (CBPI.002), in any combination.

In some embodiments, the novel N-terminal Gal-3 truncation protein includes residues 111-250 of the native Gal-3 protein, further comprising zero, one, two, three or four of the substitutions present in Gal3M1 (CBPI.002), in any combination.

In some embodiments, the novel N-terminal Gal-3 truncation protein includes residues 112-250 of the native Gal-3 protein, further comprising zero, one, two, three or four of the substitutions present in Gal3M1 (CBPI.002), in any combination.

In some embodiments, the novel N-terminal Gal-3 truncation protein includes residues 113-250 of the native Gal-3 protein, further comprising zero, one, two, three or four of the substitutions present in Gal3M1 (CBPI.002), in any combination.

In yet other embodiments, the novel N-terminal Gal-3 truncation protein includes residues 114-250, 115-250, 116-260, 117-250, 118-250, 119-250, 120-250, 121-250, 122-250, 123-250, or 124-250, wherein each such embodiment optionally comprises one, two, three, or four of the substitutions present in Gal3M1 (CBPI.002), in any combination.

In various embodiments, the N-terminal truncation proteins include, or further include, substitutions at one or more of residues 113, 114, 118, and 248 as compared to the native Gal-3 protein that are different from those substitutions found in Gal3M1. In particular embodiments, the substitutions are conservative substitutions. In some embodiments, the substitutions are semi-conservative substitutions.

In some embodiments, the N-terminal truncation proteins include, or further include, substitutions at one or more of residues 113, 114, 118, and 248 as compared to the Gal3M1 protein. In particular embodiments, the substitutions are conservative substitutions. In some embodiments, the substitutions are semi-conservative substitutions.

In various embodiments, the N-terminal truncation proteins include, or further include, at least 1, 2, 3, 4, 5 or more substitutions as compared to native Gal-3 at residues other than 113, 114, 118 and 248. In certain embodiments, the N-terminal truncation proteins include, or further include, at least 6, 7, 8, 9, or 10 or more amino acid substitutions as compared to native Gal-3 at residues other than 113, 114, 118 and 248 (numbering according to native Gal-3). In certain embodiments, the substitutions are conservative substitutions. In some embodiments, the substitutions are semi-conservative substitutions.

In typical embodiments, the N-terminal truncation protein has 70% or more, 80% or more, 85% or more, 90% or more, or 95% or more sequence identity to native Gal-3 protein. In certain embodiments, the N-terminal truncation protein has 85%, 86%, 87%, 88%, 89%, or 90% sequence identity to Gal-3 native protein. In some embodiments, the N-terminal truncation protein has 91%, 92%, 93%, 94%, or 95% sequence identity to Gal-3 native protein. In some embodiments, the N-terminal truncation protein has 96%, 97%, 98%, 99%, or 100% sequence identity to Gal-3 native protein.

In certain embodiments, the N-terminal truncation protein is produced by expression in a host cell in culture. In such embodiments, the protein can be expressed from any expressible nucleic acid that suitably encodes the desired amino acid sequence. In particular embodiments, the expressible nucleic acid encodes a protein having the amino acid sequence of SEQ ID NO:5 or SEQ ID NO:7. In specific embodiments, the expressible nucleic acid comprises a nucleic acid having the nucleic acid sequence of SEQ ID NO:6 or SEQ ID NO:8.

In various embodiments, the N-terminal truncation protein is produced by chemical synthesis rather than recombinant expression. Chemical synthesis allows one or more amino acid analogs to be incorporated into the protein sequence. In certain of these embodiments, the one or more amino acid analogs confers greater in vivo stability on the truncation protein. Chemical synthesis also allows non-peptide linkages to be introduced between amino acids, and in certain embodiments, the N-terminal truncation protein includes one or more non-peptide linkages. In particular embodiments, the non-peptide linkages confer greater in vivo stability on the truncation protein.

Thus, in a variety of embodiments, the truncation protein comprises one or more amino acid analogs. In certain embodiments, proteins include an N-terminal modification and/or a C-terminal modification to protect the protein from proteolytic degradation.

In certain embodiments, further protein sequences are fused or conjugated to the N-terminus of the truncation protein. In typical and preferred embodiments, the additional protein sequences do not confer dimerization or multimerization properties on the fusion proteins. In various embodiments, the fused amino acid sequences confer advantageous pharmacokinetic properties on the truncation protein, such as increase in serum half-life. In certain embodiments, the fused sequences confer a second binding specificity on the truncation protein, additional to its carbohydrate binding specificity. In a variety of embodiments, the fused amino acid sequences contain an epitope recognized by an antibody, such as a monoclonal antibody, bi-specific antibody, BiTE, scFv, Fab, Nanobody, single domain antibody, including antibodies to which toxins are conjugated (antibody-drug conjugates, "ADC").

In some embodiments, the N-terminal truncation protein is a peptidomimetic.

4.3.4. Polynucleotides Encoding N-Terminal Truncation Proteins

In another aspect, polynucleotides that encode the N-terminal truncation proteins described herein are provided. In some embodiments, the polynucleotides are DNA. In some embodiments, the polynucleotides are RNA.

In specific embodiments, the polynucleotides encode proteins that comprise a region having the amino sequence of SEQ ID NO:3, SEQ ID NO:5, or SEQ ID NO:7. In certain embodiments, the polynucleotides encode proteins having the amino sequence of SEQ ID NO:3, SEQ ID NO:5, or SEQ ID NO:7. In certain embodiments, the polynucleotides comprise a coding region having the polynucleotide sequence of SEQ ID NO:4, SEQ ID NO:6, or SEQ ID NO:8.

In a variety of embodiments, the polynucleotide that encodes the truncation protein is suitable for expression of the truncation protein in a host cell in culture.

In certain preferred embodiments, the encoding polynucleotide sequence is optimized, such as codon-optimized, for expression in the desired host cells. In certain embodiments, the encoding polynucleotide sequence is optimized, such as codon-optimized, for expression in mammalian cells, such CHO cells. In certain embodiments, the encoding polynucleotide sequence is optimized, such as codon-optimized, for expression in yeast cells, such as *Saccharomyces cerevisiae, Schizosaccharomyces pombe*, or *Pichia pastoris*. In some embodiments, the encoding polynucleotide sequence is optimized, such as codon-optimized, for expression in insect cells. In yet other embodiments, the encoding polynucleotide sequence is optimized, such as codon-optimized, for expression in plant cells.

In various embodiments, the expressible polynucleotide that encodes the truncation protein is operably linked to polynucleotide elements required for host cell expression. In some embodiments, the expressible polynucleotide and polynucleotide elements required for host cell expression are integrated into the nuclear genome of the host cell. In some embodiments, the expressible polynucleotide and polynucleotide elements required for host cell expression are maintained in the host cell cytoplasm.

In a variety of embodiments, the expressible polynucleotide is incorporated into an expression vector containing polynucleotide elements required for host cell expression.

In some embodiments, the expression vector is suitable for delivery of the expressible polynucleotide into host cells for expression in culture. In certain embodiments, the expression vector is suitable for delivery of the expressible polynucleotide into the cells of a human subject either ex vivo or in vivo.

5.4. Pharmaceutical Compositions

In another aspect, pharmaceutical compositions are provided that comprise a novel dominant negative Gal-3 N-terminal truncation protein as described in Section 4.3 supra, and one or more pharmaceutically-acceptable diluents, buffers, isotonifiers, carriers, excipients, stabilizing agents, preservatives, surfactants, non-ionic detergents, antioxidants, and combinations thereof.

In a variety of embodiments, the pharmaceutical composition is a liquid composition suitable for parenteral administration. In a variety of embodiments, the liquid composition is suitable for intravenous administration. In some embodiments, the liquid composition is suitable for intramuscular administration. In certain embodiments, the liquid composition is suitable for subcutaneous administration.

In some embodiments, the pharmaceutical composition comprises the Gal-3 N-terminal truncation protein at a concentration of at least 1 mg/mL, at least 5 mg/mL, or at least 10 mg/mL, 25 mg/mL, or at least 50 mg/mL. In some embodiments, the pharmaceutical composition comprises the Gal-3 N-terminal truncation protein at a concentration of at least 75 mg/mL, 100 mg/mL, 125 mg/mL, or more. In certain embodiments, the pharmaceutical composition comprises the Gal-3 N-terminal truncation protein at a concentration of no more than 150 mg/mL, no more than 125 mg/mL, or no more than 100 mg/mL. In some embodiments, the pharmaceutical composition comprises the Gal-3 N-terminal truncation protein at a concentration of no more than 75 mg/mL, or no more than 50 mg/mL.

In various embodiments, the pharmaceutical composition has a pH of 5.0-8.0, 5.5-7.5, or 6.0-7.0.

In some embodiments, the pharmaceutical composition comprises buffering agents to maintain the pH of the composition in the desired pH range. In a variety of embodiments, the buffering agents are present in a concentration of 2 mM to 50 mM, such as 2 to 40, 2 to 30, 2 to 20, 2 to 10, 10 to 50, 10 to 40, 10 to 30, 10 to 20, 20 to 50, 20 to 40, 20 to 30, or 40 to 50 mM. For example, one or more buffering agents can be present at a concentration of 2, 5, 10, 15, 20, 25, 30, 35, 40, 45, or 50 mM. Buffering agents which may be employed according to the present disclosure include both organic and inorganic acids and salts thereof, such as citrate buffers (e.g., monosodium citrate-disodium citrate mixture, citric acid-trisodium citrate mixture, citric acid-monosodium citrate mixture, and the like), succinate buffers (e.g., succinic acid-monosodium succinate mixture, succinic acid-sodium hydroxide mixture, succinic acid-disodium succinate mixture, and the like), tartrate buffers (e.g., tartaric acid-sodium tartrate mixture, tartaric acid-potassium tartrate mixture, tartaric acid-sodium hydroxide mixture, and the like), fumarate buffers (e.g., fumaric acid-monosodium fumarate mixture, fumaric acid-disodium fumarate mixture, monosodium fumarate-disodium fumarate mixture, and the like), gluconate buffers (e.g., gluconic acid-sodium gluconate mixture, gluconic acid-sodium hydroxide mixture, gluconic acid-potassium glyconate mixture, and the like), oxalate buffer (e.g., oxalic acid-sodium oxalate mixture, oxalic acid-sodium hydroxide mixture, oxalic acid-potassium oxalate mixture, and the like), lactate buffers (e.g., lactic acid-sodium lactate mixture, lactic acid-sodium hydroxide mixture, lactic acid-potassium lactate mixture, and the like) and acetate buffers (e.g., acetic acid-sodium acetate mixture, acetic acid-sodium hydroxide mixture, and the like). Furthermore, phosphate buffers, histidine buffers and trimethylamine salts such as Tris can be used.

In certain embodiments, the pharmaceutical composition is isotonic. In certain embodiments, the pharmaceutical composition is hypertonic. In some embodiments, the pharmaceutical composition is hypotonic.

In some embodiments, the pharmaceutical composition further comprises a second therapeutic agent. In such embodiments, the additional therapeutic agent is typically an antineoplastic chemotherapeutic agent. In particular embodiments, the additional therapeutic agent is selected from the group consisting of: proteasome inhibitors, e.g., selective and irreversible proteasome inhibitors such as bortezomib, carfilzomib, disulfiram, epigallocatechin-3-gallate, salinosporamide A, epoxomicin, lactacystin, MG132, ONX 0912, CEP-18770, and/or MLN9708. In certain embodiments, the additional therapeutic agent is selected from the group consisting of boron compounds, alkylating agents, antimetabolites, anthracylines, topoisomerase inhibitors, mitotic inhibitors, corticosteroids, and any combination thereof.

5.5. Methods of Treatment

In another aspect, methods of treating cancer are provided. The methods comprise administering to a subject who has cancer a therapeutically effective amount of a Gal-3 N-terminal truncation protein as described herein. In typical embodiments, the truncation protein is in a pharmaceutical composition, and the method comprises administering to a subject who has cancer a therapeutically effective amount of a pharmaceutical composition comprising a Gal-3 N-terminal truncation protein as described herein.

In certain embodiments, the Gal-3 N-terminal truncation protein is Gal3C. In other embodiments, the Gal-3 N-terminal truncation protein is a novel truncation protein as described herein. In particular embodiments, the Gal-3 N-terminal truncation protein is Gal3M1 or CBPI.001. In one embodiment, the Gal-3 N-terminal truncation protein is Gal3M1. In another embodiment, the Gal-3 N-terminal truncation protein is CBPI.001.

In various embodiments, the pharmaceutical composition is administered in an amount effective to reduce the activity in the cancer cells of at least one signal transduction pathway required for tumor growth or survival. In certain embodiments, the dominant negative Gal-3 N-terminal truncation protein is administered in an amount effective to reduce the activity of one or more of the Ras, beta-catenin, Akt, extracellular signal-regulated kinase (ERK), c-Jun N-terminal kinase (JNK), and CD44 signaling pathways.

In some embodiments, the pharmaceutical composition is administered in an amount effective to reduce the activity of the Ras signaling pathway. In particular embodiments, the pharmaceutical composition is administered in an amount effective to reduce the activity of the K-Ras signaling pathway. Gal-3 inhibits the dissociation of activated K-Ras from the plasma membrane, by a hydrophobic pocket, which accommodates the tail of K-Ras. Gal-3 multimerization is important for the activation of K-Ras, and therefore the N-terminal truncation protein inhibits K-Ras activation mediated by Galectin-3.

In some embodiments, the pharmaceutical composition is administered in an amount effective to inhibit the beta-catenin signaling pathway in cancer cells. Beta-catenin is important for the survival of cancer cells. The N-terminal truncation proteins retain binding to beta-catenin and axin, but are not phosphorylated by GSK3b since they lack the N-terminal domain, which contains the GSK3b consensus sequence, S92-XXX-S96. See, FIG. 1. The N-terminal truncation protein competes with Gal-3 for binding to the beta-catenin/axin complex, resulting in enhanced phosphorylation of beta-catenin since, unlike Gal-3, the N-terminal truncation proteins in the complex are not phosphorylated. Additionally, the N-terminal truncation protein reduces the nuclear activity of activated beta-catenin, as full-length Galectin-3 is a beta-catenin binding partner, required for the β-catenin stimulation of cyclin D1 and c-myc expression.

In some embodiments, the pharmaceutical composition is administered in an amount effective to reduce the activity of the Akt signaling pathway in cancer cells. The N-terminal truncation protein interferes with Gal3-mediated activation of AKT through PI3K, thus resulting in down-regulation of beta-catenin signaling and reduced survival of cancer cells.

In some embodiments, the pharmaceutical composition is administered in an amount effective to reduce the activity of the ERK/JNK pathway in cancer cells. Nuclear export of Gal-3 is required for the Gal-3-mediated anti-apoptotic effect in response to pro-apoptotic drugs (blockade of the intrinsic pathway), following phosphorylation of S6 by CK1. The sequences for nuclear localization and export are located in the CRD, which is retained in the N-terminal truncation proteins described herein. These N-terminal truncation proteins act as dominant negative inhibitors, competing with phosphorylated Gal-3 for export. Such competition hampers the CK1-activated export of Gal-3, and of the ERK/JNK pathway.

In some embodiments, the pharmaceutical composition is administered in an amount effect to reduce CD44 signaling in cancer cells. Gal-3 is important for CD44 signaling. CD44 expression is important in cancer and targeting CD44 eradicates cancer stem cells by interfering with bone marrow horning. CD44 functions as an endocytic receptor and endocytosis triggers the cleavage of an intracellular domain that acts as a transcription factor, resulting in enhanced CREB-mediated transcription. The CD44 intracellular domain is released from the membrane by the gamma-secretase complex, which is the same protease acting in the activation of Notch signaling. Gamma-secretase is active in endosomes after activated Notch undergoes endocytosis. Therefore, the Gal-3 N-terminal truncation protein, by preventing the formation of Galectin-3 pentamers, interferes with CD44 endocytosis and subsequently with the production of CD44 free intracellular domain. Pentameric Gal-3 mediates the endocytosis of CD44 by binding to CD44 itself and to membrane glycosphingolipids. The N-terminal truncation protein interferes with this process, reducing endocytosis of CD44 and CREB signaling in cancer cells.

In various embodiments, the cancer relies for survival and/or resistance to treatment on one or more signal transduction pathways selected from the group consisting of the Ras, beta-catenin, Akt, extracellular signal-regulated kinase (ERK), c-Jun N-terminal kinase (JNK), and CD44 signaling pathways. In some embodiments, the cancer is resistant or refractory to treatment, and administration of the Gal-3 N-terminal truncation protein alone is sufficient for treatment. In some embodiments, the cancer is resistant or refractory to treatment, and the method results in resensitization of the cancer to the prior chemotherapeutic or other treatment regimen, such as radiation therapy, to which the cancer had become resistant or refractory.

Accordingly, in certain embodiments, the N-terminal truncation protein is administered in combination with one or more additional chemotherapeutic agents and/or biological agents. Administration is said to be in combination when the N-terminal truncation protein and the one or more additional chemotherapeutic agents and/or biological agents are administered in therapeutically effective temporal proximity. In some combination embodiments, the one or more additional agents is administered at the same time as the N-terminal truncation protein. In some combination embodiments, the one or more additional agents is administered before the N-terminal truncation protein. In some combination embodiments, the one or more additional agents is administered after the N-terminal truncation protein.

In some embodiments, the one or more additional chemotherapeutic agents is selected from the group consisting of: selective and irreversible proteasome inhibitors including, but not limited to, bortezomib, carfilzomib, disulfiram, epigallocatechin-3-gallate, salinosporamide A, epoxomicin, lactacystin, MG132, ONX 0912, CEP-18770, and/or MLN9708. In certain embodiments, the additional therapeutic agent is selected from the group consisting of boron compounds, alkylating agents, antimetabolites, anthracylines, topoisomerase inhibitors, mitotic inhibitors, corticosteroids, and any combination thereof.

In some embodiments, the one or more additional chemotherapeutic agents is selected from the group consisting of: alkylating agents, antimetabolites, anthracyclines, topoisomerase inhibitors, and mitotic inhibitors.

In some embodiments, the one or more additional chemotherapeutic agents is selected from the group consisting of: venetoclax, decitabine, LY573636, aldesleukin, bortezomib, ixazomib, tipifarnib, panobinostat, pracinostat, clorfarabine, alvocidib, lenolidamide, dasatinib, volasertib, sorafenib, CP-351, vosaroxin, etoposide, mitoxantrone, guadecitabine, gemtuzumab ozogamicin, SGN-CD33A, BI 836858, AGS67E, arsenic trioxide, vorinostat, binimetinib, trametinib, BVD-523, E6201, vyxeos, AZD1775, 8-chloroadenosine, cladribine, flutarabine, capecitidine, pomalidomide, erwinaze, treosulfan, alisertib, gedatolisib, ruxolitinib, LY2606368, OXi4503, gliteritinib, sunitinib, lestaurtinib, midostaurin, quizartinib, crenolanib, pacritinib, AKN-028, FLX925, and E6201.

In some embodiments, the one or more additional chemotherapeutic agents is selected from the group consisting of: a FMS-related tyrosine kinase-3 inhibitor, a tyrosine kinase inhibitor, a proteasome inhibitor, a histone deacetylase inhibitor, a CD-33 inhibitor, a MEK inhibitor, a purine analog, an asparaginase, such as a PEGylated asparaginase, an mTOR inhibitor and an Aurora Kinase inhibitor.

In some embodiments, the one or more chemotherapeutic or biological agents is selected from the group consisting of: a kinase inhibitor, a VEGF inhibitor, a VEGFR inhibitor, a VEGFR2 inhibitor, a PDGFR inhibitor, a Src family kinase inhibitor, a hedgehog inhibitor, a retinoid X receptor activator, a histone methyltransferase inhibitor, a BCL2 inhibitor, an AKT inhibitor, a CXCR4 inhibitor, an mTOR inhibitor, an Mdm2 antagonist, an Mdm2 inhibitor, a CD25 inhibitor, a CD47 inhibitor, an IL-3R inhibitor, a BCR-Abl inhibitor, a HSP90 inhibitor, an HGF inhibitor, a MET inhibitor and a bromodomain and extra-terminal domain (BET) inhibitor and a BRD4 inhibitor.

In some embodiments, the one or more chemotherapeutic or biological agent is crizotinib, seliciclib, afatinib, aldesleukin, alemtuzumab; axitinib, belinostat, bosutinib, brentuximab vedotin, carfilzomib, ceritinib, dabrafenib, dasatinib, everolimus, ibritumomab tiuxetan, ibrutinib, sorafenib, idelalisib, ipilimumab, nilotinib, obinutuzumab, ofatumumab, panitumumab, pembrolizumab, pertuzumab, ponatinib, ramucirumab, regorafenib, romidepsin, sipuleucel, temsirolimus, tositumomab, trametinib, vandetanib, vemurafenib, vismodegib, vorinostat, ziv-aflibercept, cabozantinib, selinexnor, PF-4449913, erismodegib, GO-203-2C, thioridazine, nivolumab, bexarotene, EPZ-5676, ABT-199, GSK2141795, entospletinib, TAK-659, CPI-613, B1-8040, LY2510924, plerixafor, mozobil, OCV-501, pacritinib, eltrombopag, promacta, revolade, nintedanib, vargatef, rapamycin, MEN1112, ipilimumab, idasanutlin, R06839921, AMG-232, ADCT-301, KHK2823, CWP232291, SL-401, CC-90002, GSK2879552, lirilumab, BGB324, OTX-015, TEN-010, I-BET 762, CPI-203, CPI-0610, AG-120, AG-221, or IDH305.

In some embodiments, the one or more additional chemotherapeutic agents is bleomycin, vincristine, prednisolone, or gallium nitrate.

In certain embodiments, the cancer is multiple myeloma. In select embodiments, the N-terminal truncation protein is administered in combination with a proteasome inhibitor.

In some embodiments, the cancer is ovarian cancer.

In some embodiments, the cancer is acute myelogenous leukemia ("AML", also call acute myeloid leukemia), and the Gal-3 N-terminal truncation protein is administered in an amount effective to treat ANIL. In some embodiments, the Gal-3 N-termination truncation protein is administered in combination with one or more additional chemotherapeutic agents. In some embodiments, the additional chemotherapeutic agents are used for induction therapy. In select embodiments, the additional chemotherapeutic agents are idarubicin and cytarabine.

In some embodiments, the N-terminal truncation protein is administered in combination with radiation therapy.

In various embodiments, the cancer to be treated is a solid or hematological cancers. In some embodiments, the cancer is an advanced, and/or refractory, solid or hematological malignancy. Such cancers may include, for example, solid malignancies, including breast cancer, triple-negative breast cancer, non-small cell lung cancer, small-cell lung cancer, esophageal cancer, gastric cancer, hepatocellular carcinoma, pancreatic cancer, brain tumors, melanomas, skin cancer, prostate cancer, ovarian cancer, cervical cancer, colorectal cancer, renal-cell carcinoma, or any combination thereof. Such cancers may also include, for example, hematological malignancies including T-cell acute lymphocytic leukemia, T-cell acute lymphoblastic leukemia, T-cell chronic lymphocytic leukemia, non-Hodgkin lymphomas, Hodgkin lymphoma, multiple myeloma, plasma cell leukemia, B-cell acute lymphocytic leukemia, B-cell acute lymphoblastic leukemia, chronic myelogenous leukemia, or any combination thereof. Also, in some versions, the subject methods include a preliminary step of identifying a subject having cancer and in need of treatment for the cancer.

In a variety of embodiments, the method is effective to cause 10, 20, 30, 40, 50, 60, 70, 80, 90, 95, 96, 97, 98, 99, or 100% inhibition of activation of one of the aforementioned transduction pathways.

In another aspects, methods of treating cancer are provided, comprising administering to a subject who has cancer a therapeutically effective amount of a polynucleotide vector that expresses one or more of the truncation proteins disclosed herein. In certain such embodiments, the vector is administered by intratumoral injection.

5.6. Kits

Also provided are kits for practicing one or more of the above-described methods. The kits may be configured for use in treating cancers including Acute Myeloid Leukemia (AML) using truncated, dominant negative forms of Galectin-3.

In some embodiments, the kits include one or more of the proteins, compositions, e.g., pharmaceutical compositions, vectors and/or agents for use in the methods described herein.

The subject kits may include two or more, e.g., a plurality, three, four, five, eight, ten, etc., compositions according to any of the embodiments described herein, or any combinations thereof. The kits may also include a plurality, e.g., two, three, five or more, ten or more, twenty or more, sets of compositions, where a set of compositions is an amount of each composition required to perform the methods described herein once.

Kits may also include one or more containers, e.g., containers for storing and/or transferring the one or more compositions described herein during any of the described methods or before or after the described methods are performed. The kits, in some embodiments, also include packaging, e.g., packaging for shipping the compositions and/or containers without breaking.

In certain embodiments, the kits include instructions, such as instructions for using the subject compositions and/or performing the subject methods. The instructions are, in some aspects, recorded on a suitable recording medium. For example, the instructions may be printed on a substrate, such as paper or plastic, etc. As such, the instructions may be present in the kits as a package insert, in the labeling of the container of the kit or components thereof, e.g., associated with the packaging or sub-packaging, etc. In other embodiments, the instructions are present as an electronic storage data file present on a suitable computer readable storage medium, e.g., Portable Flash drive, CD-ROM, diskette, etc. The instructions may include complete instructions for how to use the systems or devices. The instructions may also include a website address with which instructions posted on the world wide web may be accessed.

5.7. Examples 5.7.1. Experiment Methods and Results 5.7.1.1. Cells and Treatments The human multiple myeloma cell line U266, ovarian cancer cell line SKOV3, and acute monocytic leukemia cell line THP1 were cultured in RPMI 1640 with 10% FBS. The breast cancer cell line MCF7 was cultured in Dulbecco's modified Eagle's medium (DMEM) with 10% FBS. Drugs were purchased from Merck Millipore and used at the following concentrations: Bortezomib (Bor) 5 nM; Cytarabine (Ara-c) 3.87 µM; Rapamycin (Rapa) 100 nM; Paclitaxel (Pax) 100 nM.

5.7.1.2. MTT Assay

Cells were seeded in 96-well plates, at a volume of 100 µL cell suspension/well, in quadruplicate. SKOV3 and MCF7 cells were seeded at a density of 100,000 cells/mL. THP1 cells were seeded at a density of at 200,000 cells/mL; whereas, U266 cells were seeded at a density of 300,000 cells/mL. Cells were then treated with CBPI1 or CBPI2 at 20 µg/mL for 48 hours. For the last 24 hours, the appropriate drugs were added. Cell viability was subsequently assayed after 48 hours of incubation with 0.6 mg/mL MTT ((3-(4,5-dimethylthiazolyl-2)-2,5-diphenyltetrazolium bromide; Sigma-Aldrich) for 4 hours. Formazan crystals were dissolved in 100 mL 0.01N HCL/isopropanol. Specific absorbance was measured at 570 nm with subtraction of background at 690 nm.

5.7.1.3. Detection of Apoptosis

Cells were seeded in 48-well at the same concentrations for the MTT assay. The cells were treated with CBPI1 or CBPI2 at 20 µg/mL for 48 hours. For the last 24 hours, the appropriate drugs were added. After 48 hours, the cells were washed with cold 1×PBS, resuspended in "Binding buffer 1×" (i.e., HEPES 0.01M; NaCl 0.14M; and $CaCl_2$ 2.5 mM) and incubated for 15 minutes with Annexin-V FITC (BD Biosciences)+Propidium Iodide (2.5 µg/mL final; Sigma-Aldrich) in the dark. Finally, 400 µL of Binding Buffer 1× were added to the tube and samples were processed and analyzed using the BD FACSVerse™ System (BD Biosciences).

5.7.1.4. Statistical Analysis

Data are represented as means±SD from at least three (3) independent experiments. *=P<0.001; =P<0.01; *=P<0.05.

5.7.2. Data Results

FIG. 1—provides a schematic representation of the domain structure of native Galectin-3, Gal3C, and Gal3M1.

FIG. 2—Effect of CBPI1 and CBPI2 in Ovarian Cancer.

FIG. 2 illustrates in Panel A) that CBPI2 is effective in causing apoptosis in ovarian cancer cells. Moreover, both CBPI1 and CBPI2 combined treatment with taxane-based chemotherapeutic agent Paclitaxel (Pax), significantly increases the apoptotic rate of SKOV3 cells, as compared with Paclitaxel alone. Panel B) illustrates the results MTT analysis which demonstrates that CBPI1 and CBPI2 alone, significantly decrease the viability of metabolically-active cells compared to the control cells. It should be noted that the combined effect of CBPI1/CBPI2 and Pax compared to Paclitaxel alone is not evident by MTT assay, as it measures the activity of metabolically-active cells, including those in early apoptosis.

FIG. 3—Effect of CBPI1 and CBPI2 in Multiple Myeloma.

FIG. 3 shows that Panel A) CBPI2 combined treatment with Bortezomib (Bor) significantly increase U266 cells apoptosis rate, compared with Bor alone. Panel B) MTT analysis shows that CBPI1 and CBPI2 alone significantly decrease the viability of metabolically-active cells.

FIG. 4—Effect of CBPI1 and CBPI2 in Breast Cancer.

FIG. 4 shows that Panel A) CBPI2 alone significantly increase MCF7 cells apoptotic rate, as compared to the control cells. Panel B) MTT assay shows that CBPI2 alone significantly decreases the viability of metabolically-active cells.

FIG. 5.—Effect of CBPI1 and CBPI2 in Acute Monocytic Leukemia.

Figure shows that Panel A) CBPI1 and CBPI2 in combination with Ara-C significantly increase the apoptotic rate of THP1 cells, as compared to the control cells. Panel B) MTT assay shows that CBPI2 alone significantly decreases the viability of metabolically-active cells.

FIG. 6—After the indicated treatments, the cells were analyzed for apoptosis by flow-cytometry. Plots represent the relative of fluorescence intensities in the green (FL1, horizontal axis) and red (FL2, vertical axis) channels. The apoptosis detector, Annexin-V, is linked to a green fluorescent molecule (FITC), and produces a fluorescent signal in the FL1 channel. Cells in late apoptosis are unable to pump propidium iodide (PI) out of the cytoplasm, and are therefore red fluorescent. Red fluorescence is thus picked up by the flow-cytometer in the FL2 channel. Each dot represents a fluorescent signal (cell), detected by the flow-cytometer. Each dot-plot is divided into 4 quadrants. From bottom-left and proceeding counter-clockwise, these are Q1, Q2, Q3, and Q4. Cells in Q1 are non-apoptotic (viable), as they are negative for both PI and Annexin-V. Cells in Q2 are in early apoptosis phase, as they are positive for Annexin-V but negative for PI. Cells in Q3 are positive for both PI and Annexin-V, and are therefore in late apoptotic stage. Cells in Q4 are positive for PI but negative for Annexin-X, and are therefore considered necrotic cells.

5.8. Sequence Summary

SEQ ID NO:1 Native human Gal-3 protein sequence
SEQ ID NO:2 Native human Gal-3 cDNA polynucleotide sequence
SEQ ID NO:3 Gal-3C protein sequence
SEQ ID NO:4 Gal-3C polynucleotide sequence
SEQ ID NO:5 CBPI.001 protein sequence
SEQ ID NO:6 CBPI.001 polynucleotide
SEQ ID NO:7 CBPI.002/Gal3M1 protein sequence
SEQ ID NO:8 CBPI.002/Gal3M1 polynucleotide sequence Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A truncated galectin-3 (Gal-3) protein consisting of the amino acid sequence of SEQ ID NO:7.

2. A pharmaceutical composition, comprising the protein of claim 1; and a pharmaceutically acceptable excipient.

3. The pharmaceutical composition of claim 2, further comprising a second therapeutic agent, wherein the second therapeutic is a chemotherapeutic agent.

4. A polynucleotide encoding the protein of claim 1, wherein the polynucleotide comprises the sequence of SEQ. ID NO: 8.

5. A nucleic acid vector, the vector comprising the polynucleotide of claim 4.

* * * * *

SEQUENCE LISTING

<160> NUMBER OF SEQ ID NOS: 9

<210> SEQ ID NO 1

<211> LENGTH: 250
<212> TYPE: PRT
<213> ORGANISM: Homo sapiens

<400> SEQUENCE: 1

| Met | Ala | Asp | Asn | Phe | Ser | Leu | His | Asp | Ala | Leu | Ser | Gly | Ser | Gly | Asn |
| 1 | | | | 5 | | | | | 10 | | | | | 15 | |

Pro Asn Pro Gln Gly Trp Pro Gly Ala Trp Gly Asn Gln Pro Ala Gly
            20                    25                  30

Ala Gly Gly Tyr Pro Gly Ala Ser Tyr Pro Gly Ala Tyr Pro Gly Gln
         35                    40                  45

Ala Pro Pro Gly Ala Tyr Pro Gly Gln Ala Pro Pro Gly Ala Tyr Pro
50                        55                    60

Gly Ala Pro Gly Ala Tyr Pro Gly Ala Pro Ala Pro Gly Val Tyr Pro
65                      70                    75                  80

Gly Pro Pro Ser Gly Pro Gly Ala Tyr Pro Ser Ser Gly Gln Pro Ser
         85                    90                  95

Ala Thr Gly Ala Tyr Pro Ala Thr Gly Pro Tyr Gly Ala Pro Ala Gly
            100                    105                110

Pro Leu Ile Val Pro Tyr Asn Leu Pro Leu Pro Gly Gly Val Val Pro
         115                    120                125

Arg Met Leu Ile Thr Ile Leu Gly Thr Val Lys Pro Asn Ala Asn Arg
130                      135                    140

Ile Ala Leu Asp Phe Gln Arg Gly Asn Asp Val Ala Phe His Phe Asn
145                      150                    155                160

Pro Arg Phe Asn Glu Asn Asn Arg Arg Val Ile Val Cys Asn Thr Lys
         165                    170                175

Leu Asp Asn Asn Trp Gly Arg Glu Glu Arg Gln Ser Val Phe Pro Phe
            180                    185                190

Glu Ser Gly Lys Pro Phe Lys Ile Gln Val Leu Val Glu Pro Asp His
         195                    200                205

Phe Lys Val Ala Val Asn Asp Ala His Leu Leu Gln Tyr Asn His Arg
         210                    215                220

Val Lys Lys Leu Asn Glu Ile Ser Lys Leu Gly Ile Ser Gly Asp Ile
225                      230                    235                240

Asp Leu Thr Ser Ala Ser Tyr Thr Met Ile
            245                    250

<210> SEQ ID NO 2
<211> LENGTH: 750
<212> TYPE: DNA
<213> ORGANISM: Homo sapiens

<400> SEQUENCE: 2

```
atggcagaca  attttttcgct  ccatgatgcg  ttatctgggt  ctggaaaccc  aaaccctcaa    60
ggatggcctg  cgcatggggg  gaaccagcct  gctggggcag  ggggctaccc  agggcttcc    120 tatcctgggg  cctaccccgg  gcaggcaccc  ccagggcgtt  atcctggaca  ggcacctcca   180
ggcgcctacc  ctggagcacc  tggagcttat  cccggagcac  ctgcacctgg  agtctaccca   240
gggccaccca  gcgccctggg  gcctacccca  tcttctggac  agccaagtgc  ccccggagcc   300 tacccctgcca  ctggccccta  tggcgcccct  gctgggccac  tgattgtgcc  ttataacctg   360 ccttttgcctg  ggggagtggt  gcctcgcatg  ctgataacaa  ttctgggcac  ggtgaagccc   420
aatgcaaaca  gaattgcttt  agatttccaa  agagggaatg  atgttgcctt  ccactttaac   480
ccacgcttca  atgagaacaa  caggagagtc  attgtttgca  atacaaagct  ggataataac   540
```

```
tggggaaggg aagaaagaca gtcggttttc ccatttgaaa gtgggaaacc attcaaaata    600
caagtactgg ttgaacctga ccacttcaag gttgcagtga atgatgctca cttgttgcag    660
tacaatcatc gggttaaaaa actcaatgaa atcagcaaac tgggaatttc tggtgacata    720
gacctcacca gtgcttcata taacatgata                                      750
```

```
<210> SEQ ID NO 3
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3
```

```
Gly Ala Pro Ala Gly Pro Leu Ile Val Pro Tyr Asn Leu Pro Leu Pro
1               5                   10                  15

Gly Gly Val Val Pro Arg Met Leu Ile Thr Ile Leu Gly Thr Val Lys
            20                  25                  30

Pro Asn Ala Asn Arg Ile Ala Leu Asp Phe Gln Arg Gly Asn Asp Val
        35                  40                  45

Ala Phe His Phe Asn Pro Arg Phe Asn Glu Asn Asn Arg Arg Val Ile
    50                  55                  60

Val Cys Asn Thr Lys Leu Asp Asn Asn Trp Gly Arg Glu Glu Arg Gln
65                  70                  75                  80

Ser Val Phe Pro Phe Glu Ser Gly Lys Pro Phe Lys Ile Gln Val Leu
                85                  90                  95

Val Glu Pro Asp His Phe Lys Val Ala Val Asn Asp Ala His Leu Leu
            100                 105                 110

Gln Tyr Asn His Arg Val Lys Lys Leu Asn Glu Ile Ser Lys Leu Gly
        115                 120                 125

Ile Ser Gly Asp Ile Asp Leu Thr Ser Ala Ser Tyr Thr Met Ile
    130                 135                 140
```

```
<210> SEQ ID NO 4
<211> LENGTH: 858
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
```

```
ggcgcgccgg cgggcccgct gattgtgccg tataacctgc cgctgccggg cggcgtggtg    60
ccgcgcatgc tgattaccat tctgggcacc gtgaaaccga acgcgaaccg cattgcgctg    120
gattttcagc gcggcaacga tgtggcgttt cattttaacc cgcgctttaa cgaaaacaac    180
cgccgcgtga ttgtgtgcaa caccaaactg gataacaact ggggccgcga agaacgccag    240
agcgtgtttc cgtttgaaag cggcaaaccg tttaaaattc aggtgctggt ggaaccggat    300
cattttaaag tggcggtgaa cgatgcgcat ctgctgcagt ataaccatcg cgtgaaaaaa    360
ctgaacgaaa ttagcaaact gggcattagc ggcgatattg atctgaccag cgcgagctat    420
accatgattg gcgcgccggc gggcccgctg attgtgccgt ataacctgcc gctgccgggc    480
ggcgtggtgc cgcgcatgct gattaccatt ctgggcaccg tgaaaccgaa cgcgaaccgc    540
attgcgctgg attttcagcg cggcaacgat gtggcgtttc attttaaccc gcgctttaac    600
gaaaacaacc gccgcgtgat tgtgtgcaac accaaactgg ataacaactg gggccgcgaa    660
```

```
gaacgccaga gcgtgtttcc gtttgaaagc ggcaaaccgt ttaaaattca ggtgctggtg    720
gaaccggatc attttaaagt ggcggtgaac gatgcgcatc tgctgcagta taaccatcgc    780
gtgaaaaaac tgaacgaaat tagcaaactg gcattagcg gcgatattga tctgaccagc    840
gcgagctata ccatgatt                                                  858
```

<210> SEQ ID NO 5
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Ala Pro Ala Gly Pro Leu Ile Val Pro Tyr Asn Leu Pro Leu Pro Gly
1               5                   10                  15

Gly Val Val Pro Arg Met Leu Ile Thr Ile Leu Gly Thr Val Lys Pro
            20                  25                  30

Asn Ala Asn Arg Ile Ala Leu Asp Phe Gln Arg Gly Asn Asp Val Ala
        35                  40                  45

Phe His Phe Asn Pro Arg Phe Asn Glu Asn Asn Arg Arg Val Ile Val
    50                  55                  60

Cys Asn Thr Lys Leu Asp Asn Asn Trp Gly Arg Glu Glu Arg Gln Ser
65                  70                  75                  80

Val Phe Pro Phe Glu Ser Gly Lys Pro Phe Lys Ile Gln Val Leu Val
                85                  90                  95

Glu Pro Asp His Phe Lys Val Ala Val Asn Asp Ala His Leu Leu Gln
            100                 105                 110

Tyr Asn His Arg Val Lys Lys Leu Asn Glu Ile Ser Lys Leu Gly Ile
        115                 120                 125

Ser Gly Asp Ile Asp Leu Thr Ser Ala Ser Tyr Thr Met Ile
    130                 135                 140
```

<210> SEQ ID NO 6
<211> LENGTH: 426
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
gcgccggcgg gcccgctgat tgtgccgtat aacctgccgc tgccgggcgg cgtggtgccg    60
cgcatgctga ttaccattct gggcaccgtg aaaccgaacg cgaaccgcat tgcgctggat    120
tttcagcgcg gcaacgatgt ggcgtttcat tttaacccgc gctttaacga aaacaaccgc    180
cgcgtgattg tgtgcaacac caaactggat aacaactggg gccgcgaaga acgccagagc    240
gtgtttccgt ttgaaagcgg caaaccgttt aaaattcagg tgctggtgga accggatcat    300
tttaaagtgg cggtgaacga tgcgcatctg ctgcagtata accatcgcgt gaaaaaactg    360
aacgaaatta gcaaactggg cattagcggc gatattgatc tgaccagcgc gagctatacc    420
atgatt                                                               426
```

<210> SEQ ID NO 7
<211> LENGTH: 138
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 7

Ala Val Ile Val Pro Asn Asn Leu Pro Leu Pro Gly Gly Val Val Pro
1               5                   10                  15

Arg Met Leu Ile Thr Ile Leu Gly Thr Val Lys Pro Asn Ala Asn Arg
            20                  25                  30

Ile Ala Leu Asp Phe Gln Arg Gly Asn Asp Val Ala Phe His Phe Asn
        35                  40                  45

Pro Arg Phe Asn Glu Asn Asn Arg Arg Val Ile Val Cys Asn Thr Lys
    50                  55                  60

Leu Asp Asn Asn Trp Gly Arg Glu Glu Arg Gln Ser Val Phe Pro Phe
65                  70                  75                  80

Glu Ser Gly Lys Pro Phe Lys Ile Gln Val Leu Val Glu Pro Asp His
                85                  90                  95

Phe Lys Val Ala Val Asn Asp Ala His Leu Leu Gln Tyr Asn His Arg
            100                 105                 110

Val Lys Lys Leu Asn Glu Ile Ser Lys Leu Gly Ile Ser Gly Asp Ile
            115                 120                 125

Asp Leu Thr Ser Ala Ser Tyr Asn Met Ile
    130                 135

<210> SEQ ID NO 8
<211> LENGTH: 414
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
gcggtgattg tgccgaacaa cctgccgctg ccgggcggcg tggtgccgcg catgctgatt      60
accattctgg gcaccgtgaa accgaacgcg aaccgcattg cgctggattt tcagcgcggc     120
aacgatgtgg cgtttcattt taacccgcgc tttaacgaaa acaaccgccg cgtgattgtg     180
tgcaacacca aactggataa caactggggc cgcgaagaac gccagagcgt gtttccgttt     240
gaaagcggca aaccgtttaa aattcaggtg ctggtggaac cggatcattt taaagtggcg     300
gtgaacgatg cgcatctgct gcagtataac catcgcgtga aaaaactgaa cgaaattagc     360
aaactgggca ttagcggcga tattgatctg accagcgcga gctataacat gatt           414

<210> SEQ ID NO 9
<211> LENGTH: 4
<212> TYPE: PRT
<213> ORGANISM: Homo sapiens

<400> SEQUENCE: 9

Asn Trp Gly Arg
1
```